US008936789B2

(12) United States Patent
Jiang et al.

(10) Patent No.: US 8,936,789 B2
(45) Date of Patent: Jan. 20, 2015

(54) IMMUNOENHANCER-LINKED OLIGOMERIC HIV ENVELOPE PEPTIDES

(75) Inventors: Shibo Jiang, Fresh Meadows, NY (US); Zhi Qi, Guangdong (CN); Chungen Pan, Fresh Medows, NY (US)

(73) Assignee: New York Bood Center, Inc., New York, NY (US)

( * ) Notice: Subject to any disclaimer, the term of this patent is extended or adjusted under 35 U.S.C. 154(b) by 888 days.

(21) Appl. No.: 12/581,056

(22) Filed: Oct. 16, 2009

(65) Prior Publication Data

US 2010/0098724 A1  Apr. 22, 2010

Related U.S. Application Data

(60) Provisional application No. 61/106,101, filed on Oct. 16, 2008.

(51) Int. Cl.
*A61K 39/21* (2006.01)
*A61P 31/18* (2006.01)
*C07K 14/005* (2006.01)

(52) U.S. Cl.
CPC .............. *A61K 39/21* (2013.01); *C07K 14/005* (2013.01); *C07K 2319/30* (2013.01); *C07K 2319/40* (2013.01); *C12N 2740/16122* (2013.01); *C12N 2740/16134* (2013.01)
USPC .................. 424/208.1; 424/192.1; 424/278.1

(58) Field of Classification Search
CPC ................. A61K 39/21; C07K 14/005; C12N 2710/14143; C12N 2740/16122; C12N 2740/16134
See application file for complete search history.

(56) References Cited

U.S. PATENT DOCUMENTS

| 7,144,991 | B2 | 12/2006 | Goshorn et al. |
| 7,456,251 | B2 | 11/2008 | Dwyer et al. |
| 2002/0094521 | A1 | 7/2002 | Wild et al. |
| 2004/0122214 | A1 | 6/2004 | Bray et al. |
| 2007/0122429 | A1 | 5/2007 | Kay |

FOREIGN PATENT DOCUMENTS

| WO | WO 2004009785 A2 * | 1/2004 |
| WO | 2004/104033 A2 | 12/2004 |
| WO | 2005/007831 A2 | 1/2005 |
| WO | 2006/105199 A2 | 10/2006 |
| WO | 2008/019817 A1 | 2/2008 |

OTHER PUBLICATIONS

Opalka et al. Analysis of the HIV-1 gp41 specific immune response using a multiplexed antibody detection assay. Journal of Immunological Methods 2004, vol. 287, pp. 49-65.*
Liu et al. Different from the HIV Fusion Inhibitor C34, the Anti-HIV Drug Fuzeon (T-20) Inhibits HIV-1 Entry by Targeting Multiple Sites in gp41 and gp120. The Journal of Biological Chemistry 2005, vol. 280, No. 12, pp. 11259-11273.*
Frey et al. A fusion-intermediate state of HIV-1 gp41 targeted by broadly neutralizing antibodies. Proceedings from the National Academy of Science, U.S.A, Mar. 11, 2008, vol. 105, No. 10, pp. 3739-3744.*
Eckert et al. Design of potent inhibitors of HIV-1 entry from the gp41 N-peptide region. Proceedings of the National Academy of Sciences of the United States of America 2001, vol. 98, No. 20, p. 11187-11192.*
He, Y et al. "Identification of a critical motif for the human immunodeficiency virus type 1 (HIV-1) gp41 core structure: implications for designing novel anti-HIV fusion inhibitors." J. Virol. 82:6349-6358, 2008.
Liu, S. et al. "HIV gp41 C-terminal heptad repeat contains multifunctional domains." J. Biol. Chem. 282:9612-20, 2007.
Montero, Marinieve "The Membrane-Proximal External Region of the Human Immunodeficiency Virus Type 1 Envelope: Dominant Site of Antibody Neutralization and Target for Vaccine Design." vol. 72, No. 1, Mar. 2008, pp. 54-84.
International Search Report, PCT/US2009/061088, Mailed Feb. 24, 2010.
Farzan, Michael "Stabilization of Human Immunodeficiency Virus Type 1 Envelope Glycoprotein Trimers by Disulfide Bonds Introdcued into the gp41 Glycoprotein Ectodomain." Journal of Virology, Sep. 1998, p. 7620-7627. vol. 72, No. 9.
Hellman, Ulf "Amino Acid Sequence of the Trypsin-Generated C3d Fragment from Human Complement Factor C3." Biochem J. (1985) 230, 353-361.
Louis, John M "Dsign and Properties of NCCG-gp41, a Chimeric gp41 Molecule with Nanomolar HIV Fusion Inhibitory Activity." The Journal of Biological Chemistry, vol. 276, No. 31, Issue of Aug. 3, pp. 29485-29489, 2001.
Nelson, Josh D. "Antibody Elicited Against the gp41 N-Heptad Repeat (NHR) Coiled-Coil Can Neutralize HIV-1 with Modest Potency but Non-Neutralizing Antibodies Also Bind to NHR Mimetics." Virology, Jul. 20, 2008; 377(1): 170-183.
Yang, Xinzhen "Highly Stable Trimers Formed by Human Immunodeficiency Virus Type 1 Envelope Glycoproteins Fused with the Trimeric Motif of T4 Bacteriophage Fibritin." Journal of Virology, May 2002, p. 4634-4642. vol. 76, No. 9.
Louis et al., "Covalent Trimers of the Internal N-terminal Trimeric Coiled-coil of gp41 and Antibodies Directed against them are Potent Inhibitors of HIV Envelope-mediated Cell Fusion", The Journal of Biological Chemistry, vol. 278, No. 22, 2003, pp. 20278-20285.
Munch et al., "Discovery and Optimization of a Natural HIV-1 Entry Inhibitor Targeting the gp41 Fusion Peptide." Cell, 129, 263-275, Apr. 20, 2007.
Vermeire et al., "Anti-HIV agents targeting the interaction of gp120 with the cellular CD4 receptor." Expert Opin. Investig. Drugs, 14(10): 1199-1212, 2005.

* cited by examiner

*Primary Examiner* — Louise Humphrey
(74) *Attorney, Agent, or Firm* — K&L Gates LLP; Louis C. Cullman; Michelle Glasky Bergman

(57) ABSTRACT

Provided herein are immunogenic compositions comprising fusion proteins, the fusion proteins comprising lentivirus gp41 or a fragment thereof, a trimerization or oligomerization motif and an immunoenhancer that elicit potent and broad HIV neutralizing antibody responses in the immunized hosts. Also disclosed are methods of making and using the immunogenic compositions.

15 Claims, 6 Drawing Sheets

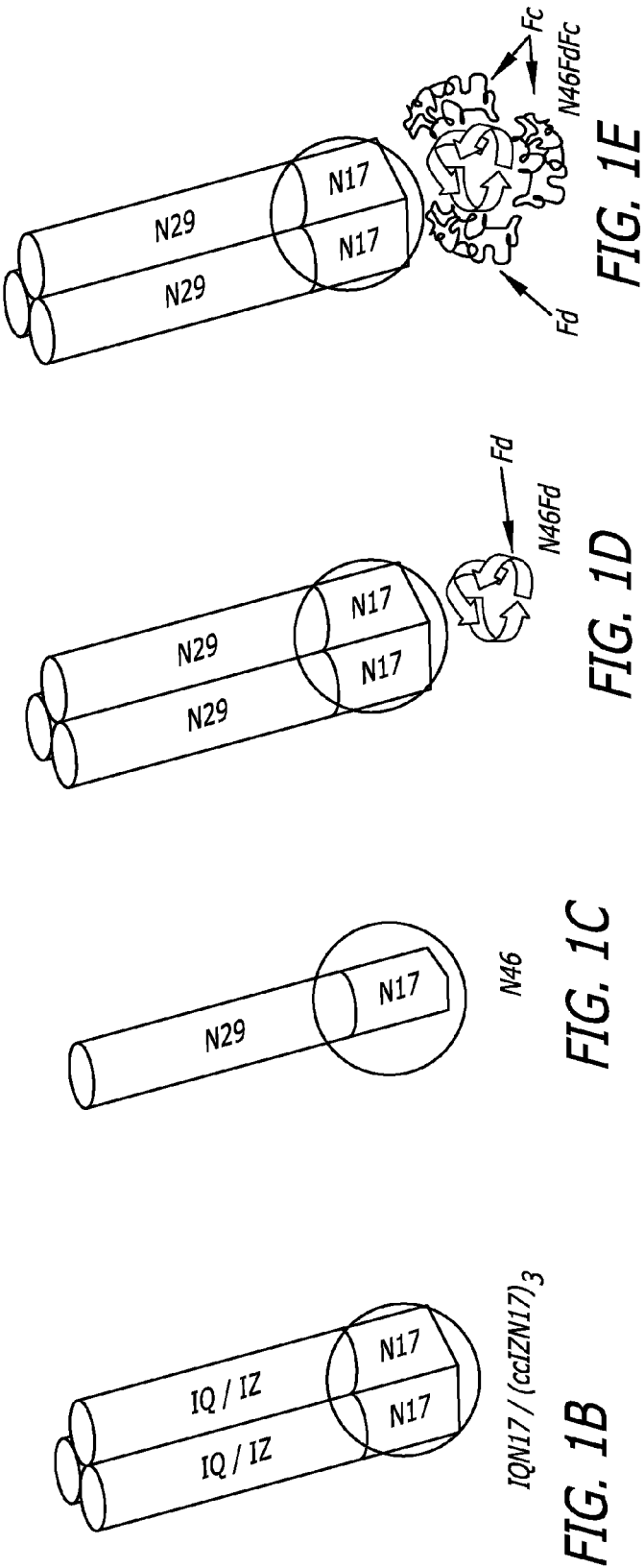

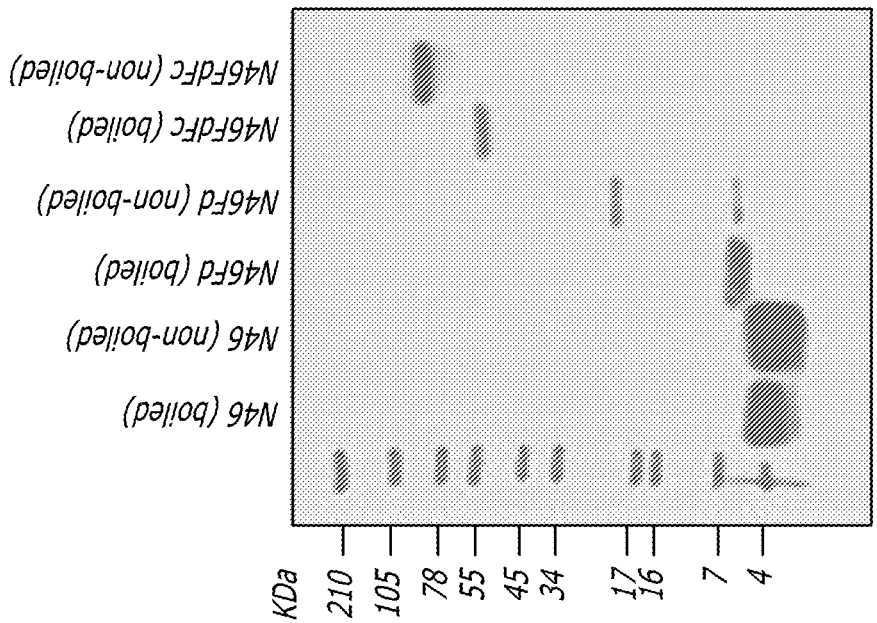
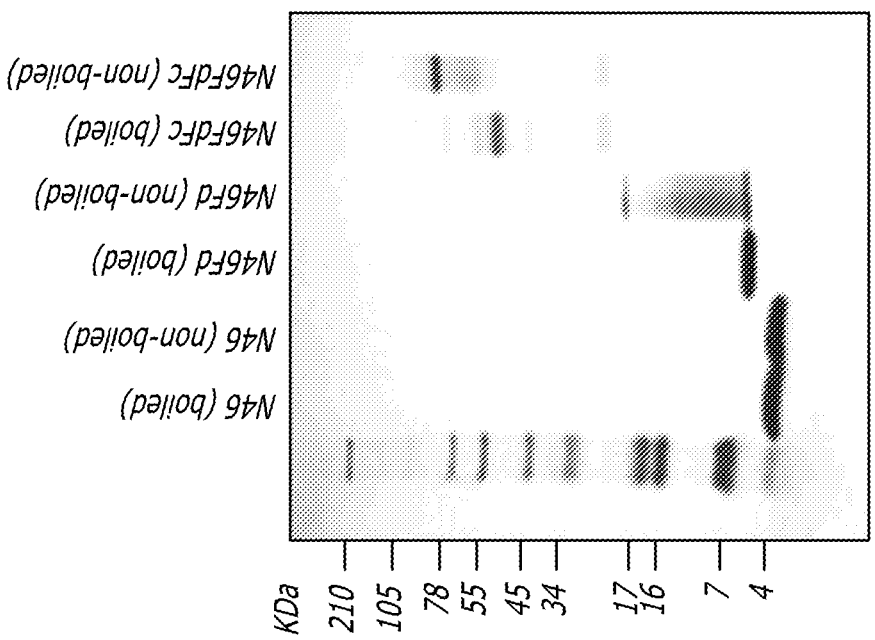
FIG. 3A
FIG. 3B

US 8,936,789 B2

IMMUNOENHANCER-LINKED OLIGOMERIC HIV ENVELOPE PEPTIDES

CROSS REFERENCE TO RELATED APPLICATION

The present application claims the benefit under 35 USC §119(e) to U.S. Provisional Patent Application 61/106,101 filed Oct. 16, 2008, the entire contents of which are incorporated by reference herein.

FIELD OF THE INVENTION

The present disclosure relates to the field of immunogenic compositions for the prevention of HIV infection.

BACKGROUND OF THE INVENTION

More than 60 million people worldwide have been infected by the human immunodeficiency virus (HIV) and nearly half have died of the resultant Acquired Immunodeficiency Syndrome (AIDS) since 1981. About 2.7 million new infections were reported in 2007. Therefore, development of an effective and safe HIV vaccine is urgently needed to contain the spread of HIV and AIDS. However, most previous efforts to achieve this goal have failed. Clinical trials of the first T-cell vaccine (Merck's MRKAd5 HIV-1 gag/pol/nef trivalent vaccine) were terminated recently because the data showed that the vaccine was unable to prevent HIV infection and could not lower virus levels in vaccinated volunteers who became infected. The first B-cell vaccine (VaxGen's AIDSVax, a bivalent gp120-based subunit vaccine) tested in clinical trials also failed to protect volunteers from HIV infection, possibly due to its inability to elicit broad neutralizing antibody responses because of great variability and high glycosylation of gp120. Since the HIV-1 envelope glycoprotein (Env) transmembrane subunit gp41 has relatively conserved sequence and less glycosylation sites than gp120, it may be a better target than gp120 for vaccine development. Indeed, two human monoclonal antibodies (mAbs) targeting gp41, 2F5 and 4E10, exhibit much broader neutralizing activity than those targeting gp120 (mAbs 2G12 and b12).

HIV-1 gp41 (SEQ ID NO. 2) plays an essential role in virus fusion with the target cell. HIV-1 pg41 consists of three essential functional regions: fusion peptide (FP), N-terminal heptad repeat (called NHR or HR1, which refer to the same sequence and are considered equivalent as used herein) and C-terminal heptad repeat (called CHR or HR2, which refer to the same sequence and are considered equivalent as used herein) (FIG. 1A). Both NHR and CHR contain a number of leucine zipper-like motifs which have tendency to form coiled coil structures. Peptides derived from the NHR and CHR regions are effective in inhibiting HIV-1 fusion with the target cells and one of the CHR-peptides, enfuvirtide was licensed by the United States Food and Drug Administration (US FDA) in 2003 as the first member of a new class of anti-HIV drugs-HIV fusion inhibitors.

HIV fusion with the host cell is initiated by binding of Env surface subunit 120 to the primary receptor CD4 and a co-receptor, CXCR4 or CCR5, resulting in a series of conformational changes in gp41, including insertion of FP into the target cell membrane and association of CHR-helices with the NHR-trimer, a prehairpin intermediate, to form a stable six-helix bundle (6-HB) core, which bring the viral envelope and target cell membrane into close proximity for fusion. X-ray crystallographic studies have shown that 6-HB consists of three molecules of a NHR-peptide that form the inner trimeric coiled-coil and three copies of a CHR-peptide that pack obliquely in an anti-parallel configuration into the highly conserved hydrophobic grooves on the surface of the internal NHR-trimer. Each groove has a deep hydrophobic pocket (FIG. 1B, circled at bottom), which plays an important role in viral fusion and maintaining the stability of the 6-HB. Accordingly, it is proposed that a CHR-peptide (e.g., enfuvirtide or C34) inhibits HIV-1 fusion by binding to the viral gp41 NHR-trimer at the fusion-intermediate state to block the formation of fusion-active core of gp41. Therefore, the gp41 NHR-trimer is a crucial target for HIV therapeutics, and may also serve as an important target for HIV vaccines.

However, the gp41 NHR-peptides cannot form stable and soluble trimers in vitro spontaneously because these peptides have tendency to aggregate in physiological solutions. To study the structure, function and immunogenicity of the gp41 prehairpin intermediate, several soluble and stable NHR-trimer mimetics have been created, including IQN17 (FIG. 1C), in which a 17-mer NHR-peptide (aa 565-581) involving in formation of the gp41 hydrophobic pocket is linked with GCN4-pI$_Q$I (IQ) motif, a soluble trimeric coiled coil, and similar mimetics with higher stability, including IZN17, IZN36 and (ccIZN17)$_3$, in which IQ is replaced with more stable trimerization motif, IZ. Other examples of NHR-trimer mimetics include NCCG-gp41, N35$_{CCG}$-N13, and 5-Helix in which one CHR peptide of the 6-HB is missing so as to expose the groove of the NHR-trimer. Although all these NHR-trimer mimetics properly present the hydrophobic groove and pocket and are effective in interacting with viral gp41 CHR to inhibit HIV-1 fusion, none of them could induce detectable neutralizing antibody responses in immunized animals. It is believed that the accessibility of the prehairpin intermediate of gp41 to antibody molecules (e.g., IgG) is limited because antisera directed against NHR-peptides exhibited no neutralizing activity at 37° C., but were effective under suboptimal temperature (31.5° C.) to prolong fusion intermediates. But interestingly, IgG1 m44, a human mAb directed against gp41 is much more potent than Fab m44 in neutralizing infection by primary HIV-1 isolates. Another human mAb, D5, that specifically binds to the pocket of NHR-trimer is highly potent to neutralize HIV-1 infection. Although rabbit antisera induced against N35$_{CCG}$-N13 showed no neutralizing activity, purified IgG from the antisera (about 5-10% of total IgGs) with high-binding affinity to the NHR-trimer could significantly inhibit HIV-1 Env-mediated cell fusion. These data suggest that the gp41 NHR-trimer in the prehairpin fusion intermediate state is accessible to antibodies, which is not restricted by either antibody size or the presence of a kinetic barrier, but may be limited by the affinity of antibodies to bind with the NHR-trimer. Therefore, it is essential to design an immunogen with proper conformation and increased immunogenicity that can induce antibodies with high-binding affinity to the gp41 prehairpin intermediate.

SUMMARY OF THE INVENTION

The N-terminal heptad repeat (NHR or HR1) alpha-helical trimer of HIV-1 envelope protein (Env) transmembrane subunit gp41 plays a crucial role in virus fusion with the target cell and represents an important target for therapeutics (e.g., enfuvirtide) and vaccines. Disclosed herein is a subunit oligomeric immunogenic composition comprising at least a portion of the HIV-1 gp41, a trimerization motif and an immunoenhancer.

In one embodiment presented herein, an immunogenic composition for induction of an immune response against a lentivirus is provided, said immunogenic composition comprising a fusion protein comprising a gp41 sequence; a trimerization or oligomerization motif; and an immunoenhancer.

In another embodiment, the gp41 sequence is from a lentivirus selected from the group consisting of HIV-1, HIV-2 or SIV. In another embodiment, the gp41 sequence is selected from a portion of the gp41 molecule selected from the group consisting of the N-terminal heptad repeat (NHR or HR1) region, the C-terminal heptad repeat (CHR or HR2) region, the fusion peptide (FP) region and the membrane proximal external region (MPER) of gp41.

In another embodiment, the trimerization or oligomerization motif is selected from the group consisting of foldon, IQ, and IZ.

In another embodiment, the immunoenhancer is selected from the group consisting of the Fc domain of immunoglobulin G, complement component C3d, and Onchocerca volvulus activation associated protein-1 (Ov-ASP-1). In another embodiment, the Fc domain of immunoglobulin G or complement component C3d is from a mammal selected from the group consisting of mouse, rabbit, pig, non-human primate and human.

In yet another embodiment, the fusion protein comprises the gp41 sequence, the trimerization or oligomerization sequence and the immunoenhancer in that order. In yet another embodiment, the fusion protein further comprises a His tag or a GST sequence.

In still another embodiment, the immunogenic composition further comprises an adjuvant.

In one embodiment disclosed herein, a method is provided for inducing an immune response to HIV comprising the steps of administering the immunogenic composition of claim 1 to a mammal in need thereof; and inducing an immune response in said mammal to said HIV.

In another embodiment, the immunogenic composition is administered by a route selected from the group consisting of subcutaneous, intramuscular, intraperitoneal, and mucous immunization. In yet another embodiment, the immune response results in the production of neutralizing antibodies in said mammal.

In one embodiment presented herein, an immunogenic composition is provided for induction of an immune response against a lentivirus comprising a fusion protein, the fusion protein comprising a N46 sequence of human immunodeficiency virus gp41; a foldon trimerization motif; and a human immunoglobulin G Fc sequence.

BRIEF DESCRIPTION OF THE DRAWINGS

FIG. 1 depicts the structures of the HIV-1 gp41 and NHR-trimers as well as the NHR- and CHR-peptides.

FIG. 3 depicts the SDS-PAGE analysis of N46, N46Fd, and N46FdhFc.

DEFINITION OF TERMS

Figure 2A:
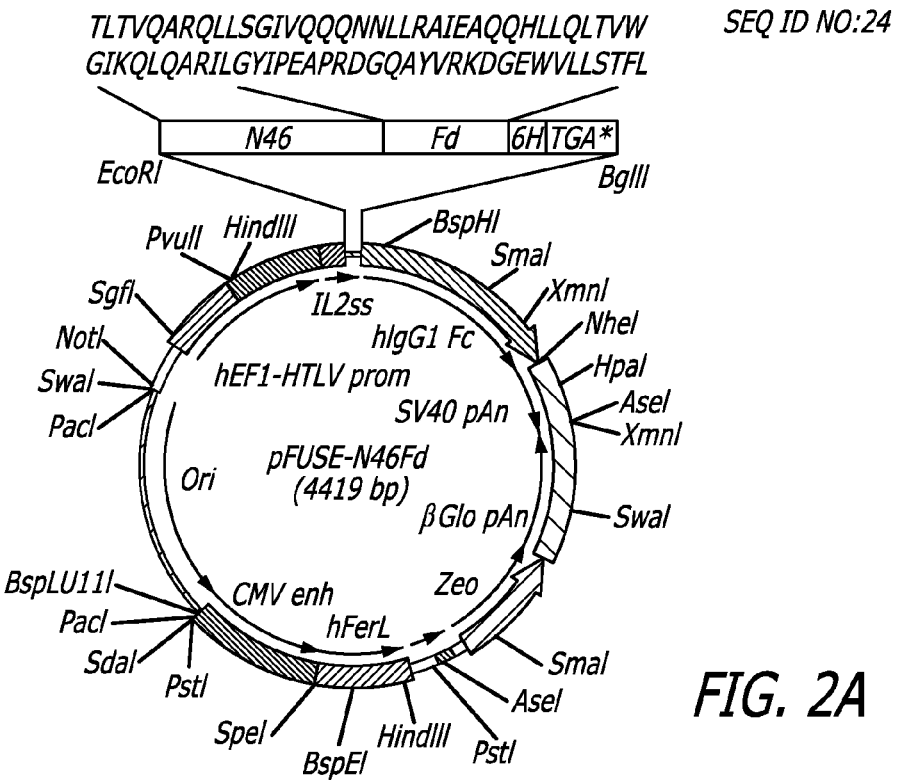
FIG. 2 depicts the map of the expression vectors pFUSE-N46Fd (FIG. 2A) and pFUSE-N46FdFc (FIG. 2B) encoding N46Fd and N46FdhFc, respectively.

To facilitate an understanding of the following Detailed Description, Examples and appended claims it may be useful to refer to the following definitions. These definitions are non-limiting in nature and are supplied merely as a convenience to the reader.

Gene: A "gene" as used herein refers to at least a portion of a genetic construct having a promoter and/or other regulatory sequences required for, or that modify the expression of, the genetic construct.

Host: As used herein "host" refers to the recipient of the present immunogenic compositions. Exemplary hosts are mammals including, but not limited to, primates, rodents, cows, horses, dogs, cats, sheep, goats, pigs and elephants. In one embodiment of the present invention the host is a human. For the purposes of this disclosure host is synonymous with "vaccinee."

Immunogen: As used herein the term "immunogen" shall mean any substrate that elicits an immune response in a host. Immunogens of the present disclosure include, but are not limited to human immunodeficiency proteins.

Immunogenic Composition: An "immunogenic composition" as used herein comprises an expressed protein or a recombinant vector, with or without an adjuvant, that expresses and/or secretes an immunogen in vivo and wherein the immunogen elicits an immune response in the host. The immunogenic compositions disclosed herein may or may not be immunoprotective or therapeutic. When the immunogenic compositions may prevent, ameliorate, palliate or eliminate disease from the host then the immunogenic composition may optionally be referred to as a vaccine. However, the term immunogenic composition is not intended to be limited to vaccines.

The term "HIV fusion" refers to a critical step of virus life cycle necessary for a virion or HIV-infected fusing with a target vesicle or cell.

"ND50" refer to the antibody concentration or antiserum titer that results in a 50% neutralization, respectively, of virus infection.

"IC50 or EC50" refer to the antibody concentration or antiserum titer that results in a 50% reduction or inhibition, respectively, in virus infection or virus-mediated cell-cell fusion.

DETAILED DESCRIPTION OF THE INVENTION

The N-terminal heptad repeat (NHR or HR1) alpha-helical trimer of HIV-1 envelope protein (Env) transmembrane subunit gp41 plays a crucial role in virus fusion with the target cell and represents an important target for therapeutics (e.g., enfuvirtide) and vaccines. Disclosed herein is a subunit immunogenic composition comprising a fusion protein comprising at least a portion of the HIV-1 gp41, a trimerization motif and an immunoenhancer. The immunogenic compositions disclosed herein may be administered in any formulations and with any adjuvant.

In one embodiment the composition comprises a fusion protein comprising an NHR-peptide N46 (SEQ ID NO. 3) derived from the HIV-1 HXB2 (subtype B) gp41 (SEQ ID NO. 2), a trimerization motif foldon (Fd) (SEQ ID NO. 18), and the human immunoglobulin G Fc domain (hFc) (SEQ ID NO. 21) as an immunoenhancer, designated N46FdhFc (SEQ ID NO. 25). The N46 peptide and the recombinant protein without Fc, N46Fd (SEQ ID NO. 24) were used as controls. Unlike the N46 peptide and N46Fd, N46FdhFc elicited potent neutralizing antibody responses in the immunized mice against infection by laboratory-adapted and primary HIV-1 strains.

In another embodiment, a fusion protein is provided comprising a gp41 NHR sequence derived from one of the following sequences: HIV-1 94UG103, subtype A (SEQ ID NO. 4); 92US657, subtype B (SEQ ID NO. 5); HIV-1 93IN101, subtype C (SEQ ID NO. 6); HIV-1 92UG001, subtype D (SEQ ID NO. 7); HIV-1 92THA009, subtype NE (SEQ ID NO. 8); HIV-1 93BR020, subtype F (SEQ ID NO. 9); HIV-1 RU570, subtype G (SEQ ID NO. 10); HIV-1 BCF02, group O (SEQ ID NO. 11); or from HIV-2 CBL20 (SEQ ID NO. 12), a trimerization motif and an immunoenhancer.

The fusion protein described herein comprises at least one gp41 NHR sequence derived from the entire NHR(HR1) region or from part of the NHR(HR1) region, e.g., N17 (SEQ ID NO. 13), N36 (SEQ ID NO. 14), N28 (SEQ ID NO. 15), N36 (SEQ ID NO. 16), N51 (SEQ ID NO. 17), or N63 (SEQ ID NO. 18) derived from HIV-1 HXB2 (subtype B).

The fusion protein described herein comprises at least one gp41 NHR(HR1) sequence from a lentivirus. Exemplary lentiviruses include, but are not limited to, any strain of HIV-1, HIV-2 or simian immunodeficiency virus (SIV).

In one embodiment, the fusion protein described herein comprises an entire gp41 sequence from HIV-1 HXB2 (SEQ ID NO. 2). In another embodiment, the fusion protein comprises an entire gp41 sequence from HIV-1, HIV-2 or SIV.

Moreover, fusion proteins disclosed herein comprise a trimerization or oligomerization motif that includes, but is not limited to, foldon (SEQ ID NO. 18), IQ (the IQ calmodulin-binding motif, SEQ ID NO. 19), and IZ (isoleucine zipper motif, SEQ ID NO. 20), Foldon is a trimerization or oligomerization motif from the T4 bacteriophage fibritin. Additionally, the gp41 component and the immunoenhancer can be physically linked by 2,2-bipyridine-5-carboxylic acid or intramolecular disulfide bonds.

Additionally, the fusion proteins include an immunoenhancer that includes, but is not limited to, Fc fragment of human IgG (SEQ ID NO. 20), mouse IgG Fc (SEQ ID NO. 21), rabbit IgG Fc (SEQ ID NO. 22), C3d of human complement, or an immunomodulator, such as a cytokine.

In one embodiment, the immunoenhancer is immunoglobulin Fc fragment. The immunoglobulin molecule consists of two light chains and two heavy chains held together by disulfide bonds such that the chains form a Y shape. The base of the Y (carboxy terminus of the heavy chain) plays a role in modulating immune cell activity. This region is called the Fc (fragment, crystallizable) region, and is composed of two heavy chains that contribute two or three constant domains depending on the class of the antibody. By binding to specific proteins, the Fc region ensures that each antibody generates an appropriate immune response for a given antigen. The Fc region also binds to various cell receptors, such as Fc receptors, and other immune molecules, such as complement proteins. By doing this, it mediates different physiological effects including opsonization, cell lysis, and degranulation of mast cells, basophils and eosinophils.

TABLE 1

Oliomeric immunogenic composition fusion protein segment sequences

| Sequence Identifier | Amino Acid Sequence |
| --- | --- |
| SEQ ID NO. 1<br>gp160 of HIV-1<br>HXB2, subtype B | MRVKEKYQHLWRWGWRWGTMLLGMLMICSATEKLWVTVYYGVPVW<br>KEATTTLFCASDAKAYDTEVHNVWATHACVPTDPNPQEVVLVNVTEN<br>FNMWKNDMVEQMHEDIISLWDQSLKPCVKLTPLCVSLKCTDLKNDTN<br>TNSSSGRMIMEKGEIKNCSFNISTSIRGKVQKEYAFFYKLDIIPIDNDTTS<br>YKLTSCNTSVITQACPKVSFEPIPIHYCAPAGFAILKCNNKTFNGTGPCT<br>NVSTVQCTHGIRPVVSTQLLLNGSLAEEEVVIRSVNFTDNAKTIIVQLNT<br>SVEINCTRPNNNTRKRIRIQRGPGRAFVTIGKIGNMRQAHCNISRAKWN<br>NTLKQIASKLREQFGNNKTIIFKQSSGGDPEIVTHSFNCGGEFFYCNST<br>QLFNSTWFNSTWSTEGSNNTEGSDTITLPCRIKQIINMWQKVGKAMYA<br>PPISGQIRCSSNITGLLLTRDGGNSNNESEIFRPGGGDMRDNWRSELY<br>KYKVVKIEPLGVAPTKAKRRVVQREKRAVGIGALFLGFLGAAGSTMGA<br>ASMTLTVQARQLLSGIVQQQNNLLRAIEAQQHLLQLTVWGIKQLQARIL<br>AVERYLKDQQLLGIWGCSGKLICTTAVPWNASWSNKSLEQIWNHTTW<br>MEWDREINNYTSLIHSLIEESQNQQEKNEQELLELDKWASLWNWFNIT<br>NWLWYIKLFIMIVGGLVGLRIVFAVLSIVNRVRQGYSPLSFQTHLPTPRG<br>PDRPEGIEEEGGERDRDRSIRLVNGSLALIWDDLRSLCLFSYHRLRDLL<br>LIVTRIVELLGRRGWEALKYWWNLLQYWSQELKNSAVSLLNATAIAVA<br>EGTDRVIEVVQGACRAIRHIPRRIRQGLERILL |
| SEQ ID NO. 2<br>gp41 of HIV-1<br>HXB2, subtype B | AVGIGALFLGFLGAAGSTMGAASMTLTVQARQLLSGIVQQQNNLLRAIE<br>AQQHLLQLTVWGIKQLQARILAVERYLKDQQLLGIWGCSGKLICTTAVP<br>WNASWSNKSLEQIWNHTTWMEWDREINNYTSLIHSLIEESQNQQEKN<br>EQELLELDKWASLWNWFNITNWLWYIKLFIMIVGGLVGLRIVFAVLSIVN<br>RVRQGYSPLSFQTHLPTPRGPDRPEGIEEEGGERDRDRSIRLVNGSLA<br>LIWDDLRSLCLFSYHRLRDLLLIVTRIVELLGRRGWEALKYWWNLLQY<br>WSQELKNSAVSLLNATAIAVAEGTDRVIEVVQGACRAIRHIPRRIRQGL<br>ERILL |
| SEQ ID NO. 3<br>N46 from gp41 of<br>HIV-1 HXB2,<br>subtype B | TLTVQARQLLSGIVQQQNNLLRAIEAQQHLLQLTVWGIKQLQARI |
| SEQ ID NO. 4<br>N46 from gp41 of<br>HIV-1 94UG103,<br>subtype A | TLTVQARQLLSGIVQQQSNLLRAIEAQQHLLKLTVWGIKQLQARVL |

TABLE 1-continued

Oliomeric immunogenic composition fusion protein segment sequences

| Sequence Identifier | Amino Acid Sequence |
|---|---|
| SEQ ID NO. 5<br>N46 from gp41 of<br>HIV-1 92US657,<br>subtype B | TLTVQARQLLSGIVQQQSNLLRAIEAQQHLLQLTVWGIKQLQARVL |
| SEQ ID NO. 6<br>N46 from gp41 of<br>HIV-1 93IN101,<br>subtype C | TLTAQARQLLSGIVQQQSNLLRAIEAQQHLLQLTVWGIKQLQTRVL |
| SEQ ID NO. 7<br>N46 from gp41 of<br>HIV-1 92UG001,<br>subtype D | TLTVQARQLLSGIVQHQNNLLMAIEAQQHLLQLTVWGIKQLQARIL |
| SEQ ID NO. 8<br>N46 from gp41 of<br>HIV-1 92THA009,<br>subtype A/E | TLTVQARQLLGIVQQQSNLLRAIEAQQHLLQLTVWGIKQLQARVL |
| SEQ ID NO. 9<br>N46 from gp41 of<br>HIV-1 93BR020,<br>subtype F | TLTVQARQLLSGIVQQQSNLLRAIEAQQHLLQLTVWGIKQLQARVL |
| SEQ ID NO. 10<br>N46 from gp41 of<br>HIV-1 RU570,<br>subtype G | TLTVQVKKLLFGIVQQQSNLLRAIEAQQHLLQLTVWGIKQLQARVL |
| SEQ ID NO. 11<br>N46 from gp41 of<br>HIV-1 BCF02, group O | ALTVRTHTLIKGIVQQQDNLLRAIQAQQQLLRLSVWGIRQLRARLL |
| SEQ ID NO. 12<br>N46 from gp41 of<br>HIV-2 CBL20 | TLSAQSRTLLAGIVQQQQQLLDVVKRQQEMLRLTVWGTKNLQARVT |
| SEQ ID NO. 13<br>N17 from gp41 of<br>HIV-1 HXB2 | LLQLTVWGIKQLQARIL |
| SEQ ID NO. 14<br>N28 from gp41 of<br>HIV-1 HXB2 | IEAQQHLLQLTVWGIKQLQARILAVERY |
| SEQ ID NO. 15<br>N36 from gp41 of<br>HIV-1 HXB2 | SGIVQQQNNLLRAIEAQQHLLQLTVWGIKQLQARIL |
| SEQ ID NO. 16<br>N51 from gp41 of<br>HIV-1 HXB2 | QARQLLSGIVQQQNNLLRAIEAQQHLLQLTVWGIKQLQARILAVERYLKQQ |
| SEQ ID NO. 17<br>N63 from gp41 of<br>HIV-1 HXB2 | STMGAASMTLTVQARQLLSGIVQQQNNLLRAIEAQQHLLQLTVWGIKQLQARILAVERYLKDQ |
| SEQ ID NO. 18<br>Foldon | GYIPEAPRDGQAYVRKDGEWVLLSTFL |
| SEQ ID NO. 19<br>IQ | RMKQIEDKIEEIESKQKKIENEIARIKK |
| SEQ ID NO. 20<br>IZ | IKKEIEAIKKEQEAIKKKIEAIEKEI |
| SEQ ID NO. 21<br>human IgG Fc | RSDKTHTCPPCPAPELLGGPSVFLFPPKPKDTLMISRTPEVTCVVVDV<br>SHEDPEVKFNWYVDGVEVHNAKTKPREEQYNSTYRVVSVLTVLHQD<br>WLNGKEYKCKVSNKALPAPIEKTISKAKGQPREPQVYTLPPSREEMTK<br>NQVSLTCLVKGFYPSDIAVEWESNGQPENNYKTTPPVLDSDGSFFLYS<br>KLTVDKSRWQQGNVFSCSVMHEGLHNHYTQKSLSLSPGK |
| SEQ ID NO. 22<br>mouse IgG Fc | RSPRGPTIKPCPPCKCPAPNLLGGPSVFIFPPKIKDVLMISLSPIVTCVV<br>VDVSEDDPDVQISWFVNNVEVHTAQTQTHREDYNSTLRVVSALPIQH<br>QDWMSGKEFKCKVNNKDLPAPIERTISKPKGSVRAPQVYVLPPPEEE |

TABLE 1-continued

Oliomeric immunogenic composition fusion protein segment sequences

| Sequence Identifier | Amino Acid Sequence |
|---|---|
| | MTKKQVTLTCMVTDFMPEDIYVEWTNNGKTELNYKNTEPVLDSDGSY<br>FMYSKLRVEKKNWVERNSYSCSVVHEGLHNHHTTKSFSRTPGK |
| SEQ ID NO. 23<br>rabbit IgG Fc | RSSKPTCPPPELLGGPSVFIFPPKPKDTLMISRTPEVTCVVVDVSQDDP<br>EVQFTWYINNEQVRTARPPLREQQFNSTIRVVSTLPIAHQDWLRGKEF<br>KCKVHNKALPAPIEKTISKARGQPLEPKVYTMGPPREELSSRSVSLTC<br>MINGFYPSDISVEWEKNGKAEDNYKTTPAVLDSDGSYFLYSKLSVPTS<br>EWQRGDVFTCSVMHEALHNHYTQKSISRSPGK |
| SEQ ID NO. 24<br>N46Fd | TLTVQARQLLSGIVQQQNNLLRAIEAQQHLLQLTVWGIKQLQARILGYIP<br>EAPRDGQAYVRKDGEWVLLSTFL |
| SEQ ID NO. 25<br>N46hFc | TLTVQARQLLSGIVQQQNNLLRAIEAQQHLLQLTVWGIKQLQARILRSD<br>KTHTCPPCPAPELLGGPSVFLFPPKPKDTLMISRTPEVTCVVVDVSHE<br>DPEVKFNWYVDGVEVHNAKTKPREEQYNSTYRVVSVLTVLHQDWLN<br>GKEYKCKVSNKALPAPIEKTISKAKGQPREPQVYTLPPSREEMTKNQV<br>SLTCLVKGFYPSDIAVEWESNGQPENNYKTTPPVLDSDGSFFLYSKLT<br>VDKSRWQQGNVFSCSVMHEGLHNHYTQKSLSLSPGK |
| SEQ ID NO. 26<br>N46FdhFc | TLTVQARQLLSGIVQQQNNLLRAIEAQQHLLQLTVWGIKQLQARILGYIP<br>EAPRDGQAYVRKDGEWVLLSTFLRSDKTHTCPPCPAPELLGGPSVFL<br>FPPKPKDTLMISRTPEVTCVVVDVSHEDPEVKFNWYVDGVEVHNAKT<br>KPREEQYNSTYRVVSVLTVLHQDWLNGKEYKCKVSNKALPAPIEKTIS<br>KAKGQPREPQVYTLPPSREEMTKNQVSLTCLVKGFYPSDIAVEWESN<br>GQPENNYKTTPPVLDSDGSFFLYSKLTVDKSRWQQGNVFSCSVMHE<br>GLHNHYTQKSLSLSPGK |
| SEQ ID NO. 27<br>N46FdmFc | TLTVQARQLLSGIVQQQNNLLRAIEAQQHLLQLTVWGIKQLQARILGYIP<br>EAPRDGQAYVRKDGEWVLLSTFLRSDKTHTCPPCPAPELLGGPSVFL<br>FPPKPKDTLMISRTPEVTCVVVDVSHEDPEVKFNWYVDGVEVHNAKT<br>KPREEQYNSTYRVVSVLTVLHQDWLNGKEYKCKVSNKALPAPIEKTIS<br>KAKGQPREPQVYTLPPSREEMTKNQVSLTCLVKGFYPSDIAVEWESN<br>GQPENNYKTTPPVLDSDGSFFLYSKLTVDKSRWQQGNVFSCSVMHE<br>GLHNHYTQKSLSLSPGK |
| SEQ ID NO. 28<br>N46FdrFc | TLTVQARQLLSGIVQQQNNLLRAIEAQQHLLQLTVWGIKQLQARILGYIP<br>EAPRDGQAYVRKDGEWVLLSTFLRSDKTHTCPPCPAPELLGGPSVFL<br>FPPKPKDTLMISRTPEVTCVVVDVSHEDPEVKFNWYVDGVEVHNAKT<br>KPREEQYNSTYRVVSVLTVLHQDWLNGKEYKCKVSNKALPAPIEKTIS<br>KAKGQPREPQVYTLPPSREEMTKNQVSLTCLVKGFYPSDIAVEWESN<br>GQPENNYKTTPPVLDSDGSFFLYSKLTVDKSRWQQGNVFSCSVMHE<br>GLHNHYTQKSLSLSPGK |
| SEQ ID NO. 29<br>IQN46 | RMKQIEDKIEEIESKQKKIENEIARIKKTLTVQARQLLSGIVQQQNNLLR<br>AIEAQQHLLQLTVWGIKQLQARIL |
| SEQ ID NO. 30<br>IQN46hFc | RMKQIEDKIEEIESKQKKIENEIARIKKTLTVQARQLLSGIVQQQNNLLR<br>AIEAQQHLLQLTVWGIKQLQARILRSDKTHTCPPCPAPELLGGPSVFLF<br>PPKPKDTLMISRTPEVTCVVVDVSHEDPEVKFNWYVDGVEVHNAKTK<br>PREEQYNSTYRVVSVLTVLHQDWLNGKEYKCKVSNKALPAPIEKTISK<br>AKGQPREPQVYTLPPSREEMTKNQVSLTCLVKGFYPSDIAVEWESNG<br>QPENNYKTTPPVLDSDGSFFLYSKLTVDKSRWQQGNVFSCSVMHEGL<br>HNHYTQKSLSLSPGK |
| SEQ ID NO. 31<br>IZN46 | IKKEIEAIKKEQEAIKKKIEAIEKEITLTVQARQLLSGIVQQQNNLLRAIEA<br>QQHLLQLTVWGIKQLQARIL |
| SEQ ID NO. 32<br>IZN46hFc | IKKEIEAIKKEQEAIKKKIEAIEKEITLTVQARQLLSGIVQQQNNLLRAIEA<br>QQHLLQLTVWGIKQLQARILRSDKTHTCPPCPAPELLGGPSVFLFPPK<br>PKDTLMISRTPEVTCVVVDVSHEDPEVKFNWYVDGVEVHNAKTKPRE<br>EQYNSTYRVVSVLTVLHQDWLNGKEYKCKVSNKALPAPIEKTISKAKG<br>QPREPQVYTLPPSREEMTKNQVSLTCLVKGFYPSDIAVEWESNGQPE<br>NNYKTTPPVLDSDGSFFLYSKLTVDKSRWQQGNVFSCSVMHEGLHNH<br>YTQKSLSLSPGK |

As used herein, nucleotide sequences which are substantially the same share at least about 90% identity, and amino acid sequences which are substantially the same typically share more than 95% amino acid identity. It is recognized, however, that proteins (and DNA or mRNA encoding such proteins) containing less than the above-described level of homology arising as splice variants or that are modified by conservative amino acid substitutions (or substitution of degenerate codons) are contemplated to be within the scope of the present disclosure. As readily recognized by those of skill in the art, various ways have been devised to align sequences for comparison, e.g., Blosum 62 scoring matrix, as described by Henikoff and Henikoff in Proc. Natl. Acad. Sci. USA 89:10915 (1992). Algorithms conveniently employed for this purpose are widely available (see, for example, Needleman and Wunsch in J. Mol. Bio. 48:443 (1970).

Therefore, disclosed herein are amino acid sequences 85%, 90%, 95%, 98%, 99% or 100% identical to SEQ ID NOs:1-32.

Also disclosed herein are conservative amino acid substitutions of amino acids sequences SEQ ID NOs:1-32. Conservative amino acids substitutions are defined as changed, which although they alter the primary sequence of the protein or peptide, do not normally alter its function. Conservative amino acid substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

In one embodiment, the claimed fusion proteins can be constructed using overlapping primers. In another embodiment, the DNA sequence (GGCTATATTCCG GAAGCGC-CGCGTGATGGCCAGGCGTATGTGCG-TAAAGATGGCGAATGGGTGCTG CTGTCTACCTTTCTG; SEQ ID NO:36) encoding Fd (aa sequence: GYIPEAPRDG QAYVRKDGEWVLLSTFL) is synthesized first. Separate PCR products of the gp41 sequence and Fd are generated and the gp41 segment-Fd fusion fragment is amplified by one-round PCR using a gp41 forward primer and Fd reverse primer with gp41 (or a fragment thereof) and Fd DNA (PCR products) as templates. The amplified gp41 segment-Fd PCR product is then inserted into the hFc vector, to get an gp41-Fd-hFc recombinant plasmid encoding gp41-Fd-hFc fusion proteins. For the purposes of this discussion, the term "gp41" or "gp41 component" refers to the full-length gp41 protein, or a fragment thereof.

The gp41 component (gp41), trimerization or oligomerization motif component (TM) and the immunoenhancer component (IE) of the fusion proteins can be constructed in a variety of orientations including, but not limited to, gp41-TM-IE, gp41-IE-TM, IE-gp41-TM, TM-gp41-IE, etc. In one embodiment, the components are arranged gp41-TM-IE.

In one embodiment, pFUSE-hIgG1-Fc (human Fc, hFc), pFUSE-mIgG2a-Fc2 (murine Fc, mFc), or pFUSE-rIgG2-Fc2 (rabbit Fc, rFc) vectors are used for construction of the disclosed fusion proteins. In another embodiment, the fusion proteins can be expressed from other mammalian cell expression vectors, including, but not limited to, pcDNA3.1, pcDNA6-His, PEE13.1, PEE1.41, pCMV-NEO-BAM, pSV2, and pCMV1,2,3,4,5,6. In another embodiment, the fusion proteins can be expressed from insect cell expression vectors including, but not limited to, pAcGP67, pFastBac Dual, and pMT/V5-His-TOPO. In yet another embodiment, the fusion proteins can be expressed from E. coli expression vectors including, but not limited to, pET, pET-SUMO, and pGEX vectors with GST.

The following expression systems are suitable for use in expressing the disclosed fusion proteins: mammalian cell expression systems such as, but not limited to, pcDNA expression system, and GS Gene expression system; insect cell expression systems such as, but not limited to, Bac-to-Bac expression system, baculovirus expression system and DES expression systems; and E. coli expression systems including, but not limited to, pET, pSUMO and GST expression systems.

Advantages of proteins expressed in mammalian cell expression systems include the follows. The mammalian cell expression system is a relatively mature eukaryotic system for expression of recombinant proteins. There is a far higher chance to get correctly folded soluble proteins with proper glycosylation, making the expressed protein maintain native conformation and keep sufficient bioactivity if necessary. This system can either transient or stable express recombinant antigens, and promote signal synthesis. Recombinant proteins expressed in this way may keep good antigenicity and immunogenicity. However, both insect and bacterial expression systems provide inexpensive and efficient expression of active proteins, particularly when glycosylation is not required for bioactivity.

The purification systems are dependent on whether a tag is linked or fused with the fusion proteins. When the fusion proteins are fused with IgG Fc vectors, Protein A or Protein G affinity chromatography is used for the purification. If the fusion proteins are fused with GST proteins, the GST columns will be used for the purification. If the fusion proteins link with 6×His tag at the N- or C-terminal, the expressed proteins are be purified using His tag columns. If no tag is linked with recombinant proteins, the expressed proteins re be purified using Fast protein liquid chromatography (FPLC), High performance liquid chromatography (HPLC) or other chromatographies.

In certain embodiments, the immunogenic compositions further comprise an adjuvant. Adjuvants suitable for use in animals include, but are not limited to, Freund's complete or incomplete adjuvants, Sigma Adjuvant System (SAS), and Ribi adjuvants. Adjuvants suitable for use in humans include, but are not limited to, MF59 (an oil-in-water emulsion adjuvant), aluminum hydroxide, -phosphate or -oxide, HAVLO-GEN® (an acrylic acid polymer-based adjuvant, Intervet Inc., Millsboro, Del.), polyacrylic acids, oil-in-water or water-in-oil emulsion based on, for example a mineral oil, such as BAYOL™ or MARCOL™ (Esso Imperial Oil Limited, Canada), or a vegetable oil such as vitamin E acetate, saponins, and Onchocerca volvulus activation-associated protein-1 (ASP-1) (see US 20060039921, which is incorporated by reference herein for all it discloses regarding ASP-1 adjuvants). However, components with adjuvant activity are widely known and, generally, any adjuvant may be utilized that does not adversely interfere with the efficacy or safety of the vaccine and/or immunogenic composition.

Vaccine and immunogenic compositions according to the various embodiments disclosed herein can be prepared and/or marketed in the form of a liquid, frozen suspension or in a lyophilized form. Typically, vaccines and/or immunogenic compositions prepared according to the present disclosure contain a pharmaceutically acceptable carrier or diluent customarily used for such compositions. Carriers include, but are not limited to, stabilizers, preservatives and buffers. Suitable stabilizers are, for example SPGA, Tween compositions (such as are available from A.G. Scientific, Inc., San Diego, Calif.), carbohydrates (such as sorbitol, mannitol, starch, sucrose, dextran, glutamate or glucose), proteins (such as dried milk serum, albumin or casein) or degradation products thereof. Non-limiting examples of suitable buffers include alkali metal phosphates. Suitable preservatives are thimerosal, merthiolate and gentamicin. Diluents include water, aqueous buffer (such as buffered saline), alcohols and polyols (such as glycerol).

Also disclosed herein are methods for inducing an immune response to HIV using the disclosed fusion proteins. Generally, the vaccine or immunogenic composition may be administered subcutaneously, intradermally, submucosally, or intramuscularly in an effective amount to prevent infection from HIV and/or treat an infection with HIV. An effective amount is defined as an amount of immunizing fusion protein that will induce immunity in the vaccinated animals, against challenge by a virulent virus. Immunity is defined herein as the induction of a significant higher level of protection in a population of the animal after vaccination compared to an unvaccinated group.

Further, in various formulations of the vaccines and/or immunogenic compositions, suitable excipients, stabilizers and the like may be added.

EXAMPLES

Example 1

Design of Immunoenhancer-Linked HIV-1 gp41 NHR-Trimer-Based Vaccine

As shown in FIG. 1A, the HIV-1 HXB2 gp41 consists of an ectodomain, a transmembrane (TM) and cytoplasmic (CP) domains. The ectodomain contains: fusion peptide (FP); N-terminal heptad repeat (NHR), which has a pocket-forming sequence (underlined); Immunodominant (ID) loop; C-terminal heptad repeat (CHR), which contains a pocket-binding sequence (underlined); and a membrane proximal external region (MPER). The residue numbers of each region correspond to their positions in gp160 of HIV-1 HXB2. FIGS. 1B-E show the gp41 NHR-trimeric structures: B) IQN17 and (ccIZN17)$_3$, which consists of a 17-mer pocket-forming sequence and a trimerization motif, GCN4-pIQI (IQ) or IZ; C) N46, a NHR-peptide (residues 536-581) containing the N17 pocket-forming sequence; D) N46Fd, a recombinant protein consisting of N46 and foldon (Fd), a trimerization motif; and E) N46FdhFc, a recombinant protein containing N46Fd and human IgG Fc. The conserved hydrophobic pocket is circled.

Example 2

Construction of Plasmids Encoding N46Fd and N46FdhFc

Figure 2B:
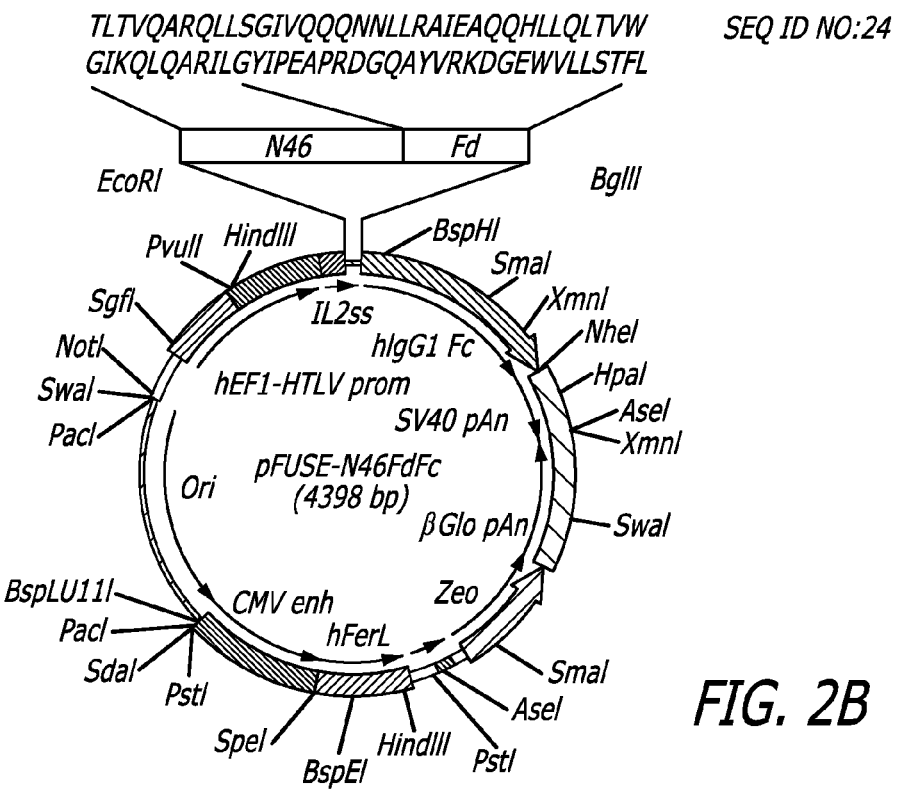

The N46 sequence was derived from the NHR region of HIV-1 HXB2 gp41. The pHXB2-env plasmid was employed as a template to synthesize a DNA fragment encoding the N46 amino acid sequence. All primers and the DNA fragment encoding the Fd sequence were synthesized by Integrated DNA Technologies (Coralville, Iowa). The N46 DNA fragment was then linked with Fd DNA fragment using an overlapping primer design program. The N46Fd DNA fragment was applied as the template for PCR amplification using the forward primer 5'-CCGGAATTCGACGCTGACGGTA-CAGG-3' (SEQ ID NO:33) and the reverse primer 5'-GGAA-GATCTTCAGTGGTGGTGGTG GTGGTGCAGAAAGG-TAGA-3' (SEQ ID NO:34). The amplified N46Fd DNA fragment was digested by EcoRI and BglII and inserted into the vector pFUSE-hIgG1-Fc2, designated pFUSE-N46Fd and encoded the N46Fd fusion protein. Subsequently, the pFUSE-N46FdFc plasmid DNA encoding the N46FdhFc protein was constructed using the same method of preparation for pFUSE-N46Fd with the following exceptions: (i) the pFUSE-N46Fd instead of the pHXB2-N46Fd plasmid was used as the template, and (ii) the following reverse primer was used: 5'-GGAAGATCTCAGAAAGGTAGACAG-3' (SEQ ID NO:35; containing no stop codon). The sequences of all constructs were confirmed by DNA sequencing. FIG. 2 shows the maps of the plasmids encoding N46Fd (A) and N46FdhFc (B). "6H" and "TGA*" represent 6-His tag and stop codon, respectively.

Example 3

Expression of N46Fd and N46FdhFc in Mammalian Cells and *E. Coli*

The plasmids of pFUSE-N46Fd and pFUSE-N46FdhFc were transformed into DH5α cells. A single colony from freshly streaked selective plate containing 25 μg/ml Zeocin was picked and inoculated in a starter culture of 5 ml LB medium containing 25 μg/ml Zeocin with shaking at 250 rpm for 8 hrs at 37° C. Then 2 ml of the starter culture supernatants was applied to 400 ml LB containing 25 μg/ml Zeocin. After incubation overnight at 37° C., the broth was centrifuged at 6,000 rpm (4,500×g) for 15 min. The plasmid was purified using a Plasmid Purification Kit (QIAGEN, Valencia, Calif.) and then transfected to 293T cells using Lipofectamine 2000 reagent (Invitrogen, Carlsbad, Calif.) according to the manufacturer's protocol. Fresh DMEM was supplied next day. N46Fd and N46FdhFc were purified as described above.

For expression of N46FdhFc in *E. coli*, the plasmids pGEX-N46Fd and pGEX-N46FdFc were transformed into Rosetta 2 (DE3) LysS complete cells, respectively, which were incubated in LB medium containing 100 μg/ml ampicillin at 37° C. overnight. One colony was selected and transferred to 5 ml of LB medium. After incubation at 37° C. for 16 hrs, 2 ml culture supernatants were collected and transferred to 400 ml LB containing 100 μg/ml ampicillin and 0.5 mM IPTG to induce protein expression. After culture for 4 hrs, the pellets were collected after centrifugation at 6,000 rpm (4,500×g) for 20 min, and then sonicated three times (10 min each time). After centrifugation at 14,000 rpm (20,000×g) for 30 min and filtration with 0.45 μm membrane, the supernatants were passed through a GST-binding column and the GST-tag was removed by treatment with PreScission Protease (GE Healthcare, N.J.). N46Fd was purified by using a Ni-NTA His-Bind Superflow column since the foldon fragment in N46Fd can bind with his-binding beads. N46FdhFc was further purified by loading the eluated fractions to Protein A-Sepharose 4 Fast Flow column (Amerhsam Biosciences, Piscataway, N.J.). After washing, N46FdhFc was eluted with glycine-HCl buffer (pH 2.7) and neutralized with 1 M Tris-HCl buffer (pH 9), which was replaced by PBS using 10 kd filter (Millipore Corporation, Billerica, Mass.) through centrifugation at 2,900 rpm (2,003×g) for 3 times and 20 min for each time. The purified protein was stored at −4° C. until use.

Example 4

Characterization of N46, N46Fd and N46FdhFc

The recombinant fusion proteins N46Fd and N46FdhFc as well as the synthetic peptide N46 were analyzed by SDS-PAGE, acid native PAGE, and Western blot. Purified N46, N46Fd and N46FdhFc (boiled and unboiled) were analyzed by SDS-PAGE using 10-20% Tris-Tricine Gradient Gels (Invitrogen). The peptide or proteins were also analyzed by acid native PAGE as described by Sackett et al. (J. Biol. Chem. 281(31):21755-62, 2006). Briefly, 10% polyacrylamide continuous native gels at pH 3.4 were prepared using 30 mM β-alanine and 42 mM formic acid and pre-run in the same buffer containing 100 μM TCEP as a reducing agent. Gel electrophoresis was performed with a constant voltage of 125 V at room temperature for 2 h. The gel was then stained with Coomassie blue and imaged with a FluorChem 8800 imaging system (Alpha Innotech Corp., San Leandro, Calif.). For western-blotting, the peptide or proteins within the gels after separation by SDS-PAGE or acid native PAGE were transferred onto a 0.45 μm-pore nitrocellulose membrane (Amersham Pharmacia Biotech, UK) at 100 V for 2 h and then 60 V for 1 h. The blotted membranes were rinsed with PBST (PBS with 0.1% Tween 20) three times for 5 min and then blocked in fresh PBST containing 5% non-fat dried milk at 4° C. overnight. After several washes, the membranes were incubated in rabbit anti-N46 IgG (1 μg/ml). HRP-conjugated goat anti-rabbit IgG (for anti-N46) and the ECL substrate solution (Amersham) were added sequentially. The blots were then visualized with autoradiography films.

Figures 4A, 4B:
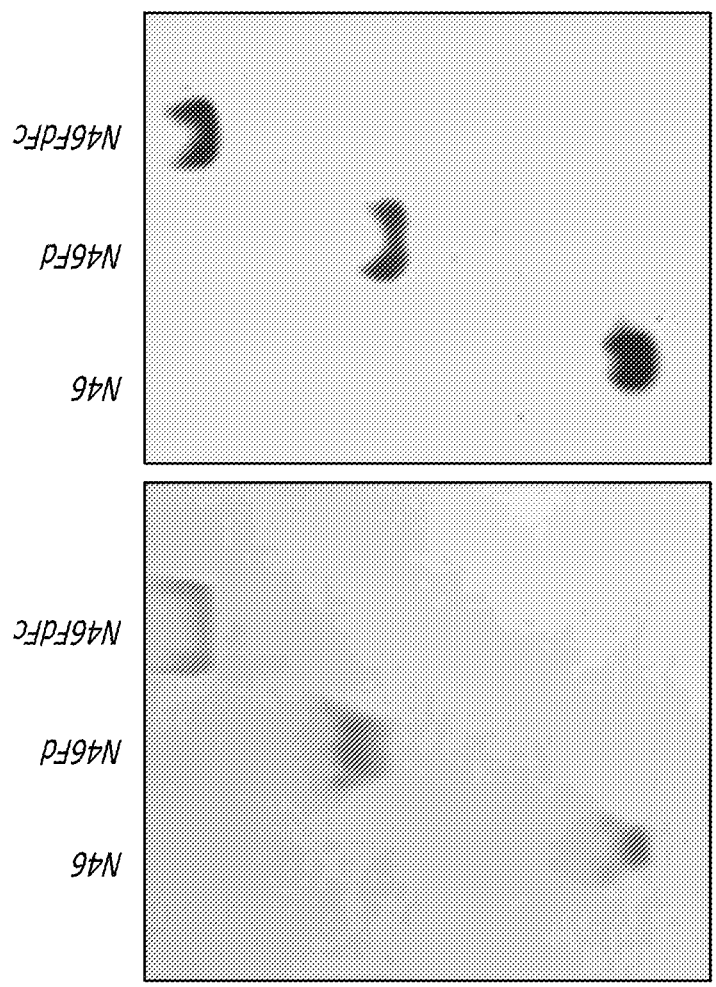
FIG. 4 depicts the analysis of N46, N46Fd, and N46FdhFc by using Acid-N-PAGE (FIG. 4A) and Western blot (FIG. 4B) using anti-N46 antibodies.

As shown in FIG. 3A, without boiling, N46Fd was found in trimeric and monomeric forms, while N46FdhFc was found mainly in trimeric form under reducing condition because the Fd-stabilized trimer is resistant to reducing reagent. With boiling, N46Fd and N46FdhFc were mainly in monomeric and dimeric forms, respectively. N46 was in monomeric form under reducing condition with or without boiling. All the major bands reacted with polyclonal anti-N46 antibodies by Western blots (FIG. 3B). N46, N46Fd and N46FdhFc displayed no bands in native PAGE because they contain a net positive charge, while each of them showed a single band in acid native PAGE (stained with Coomassie blue) (FIG. 4A). All three immunogens reacted with rabbit anti-N46 antibodies by Western blots (FIG. 4B). These results suggest that N46Fd and N46FdhFc are in trimeric or other oligomeric forms.

Example 5

N46FdhFc Induced Potent Neutralizing Antibodies Against HIV-1

Balb/c mice (6-8 weeks old, 5 mice/group) were immunized subcutaneously with N46 peptide, recombinant N46Fd or N46FdhFc, in the presence of complete Freund's adjuvant (CFA, Sigma) and boosted three times with the same antigen plus incomplete Freund's adjuvant (IFA) as outline in Table 2:

TABLE 2

Mouse immunization procedure

| Day | Procedure |
|---|---|
| 0 | Prebleed, primary immunization, s.c. injection of 20 µg of an antigen with CFA |
| 30 | Boost, s.c. injection of 10 µg of an antigen with IFA |
| 50 | Boost, i.p. injection of 10 µg of an antigen in PBS |
| 57 | Boost, i.p. injection of 10 µg of an antigen in PBS |
| 64 | Terminal bleed |

All sera were heat-inactivated at 56° C. for 30 min and kept at 4° C. until use.

Figure 5:
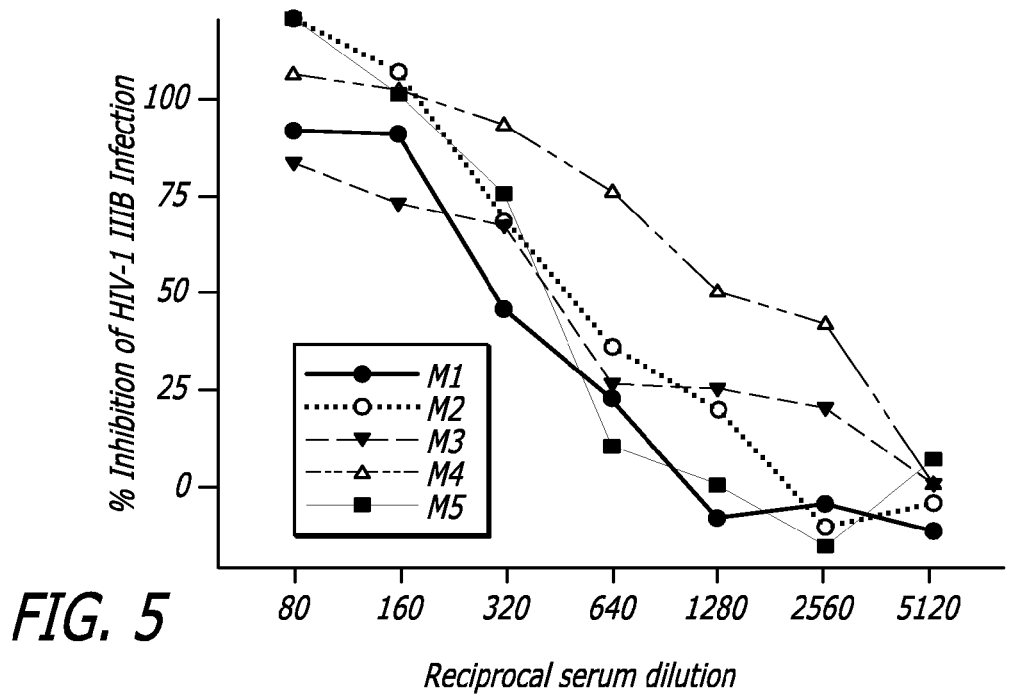
FIG. 5 depicts neutralization of HIV-1 IIIB (X4) Bal (R5) infection mediated by antisera against N46FdhFc.

Balb/c mice were immunized with adjuvant and N46, N46Fd or N46FdhFc and individual mouse serum was collected seven days after the last boost and tested for neutralizing activity against HIV-1 IIIB infection by the XTT assay for measuring HIV-1-mediated CPE. The XTT assay was conducted as previously described in Jiang et al. (J. Exp. Med. 174, 1557-1563, 1991). Briefly, MT-2 cells were infected with HIV-1 IIIB strain at 100 $TCID_{50}$ (50% tissue culture infective dose) in RPMI 1640 medium containing 10% FBS in the presence or absence of an antibody or antiserum at a series of 2-fold dilution at 37° C. overnight. The culture supernatants were then removed and fresh media were added. On day 6 post-infection, 50 µl of XTT solution (1 mg/ml) containing 0.02 µM of phenazine methosulphate (PMS) was added. After 4 hrs, absorbance at 450 nm (A450) was measured with an ELISA reader and the ND50 values were calculated as described above. As shown in FIG. 5 and Table 3, sera from mice immunized with N46 and N46Fd exhibited no detectable inhibitory activity, while sera from all the five mice vaccinated with N46FdhFc exhibited potent neutralizing activity.

Figure 6:
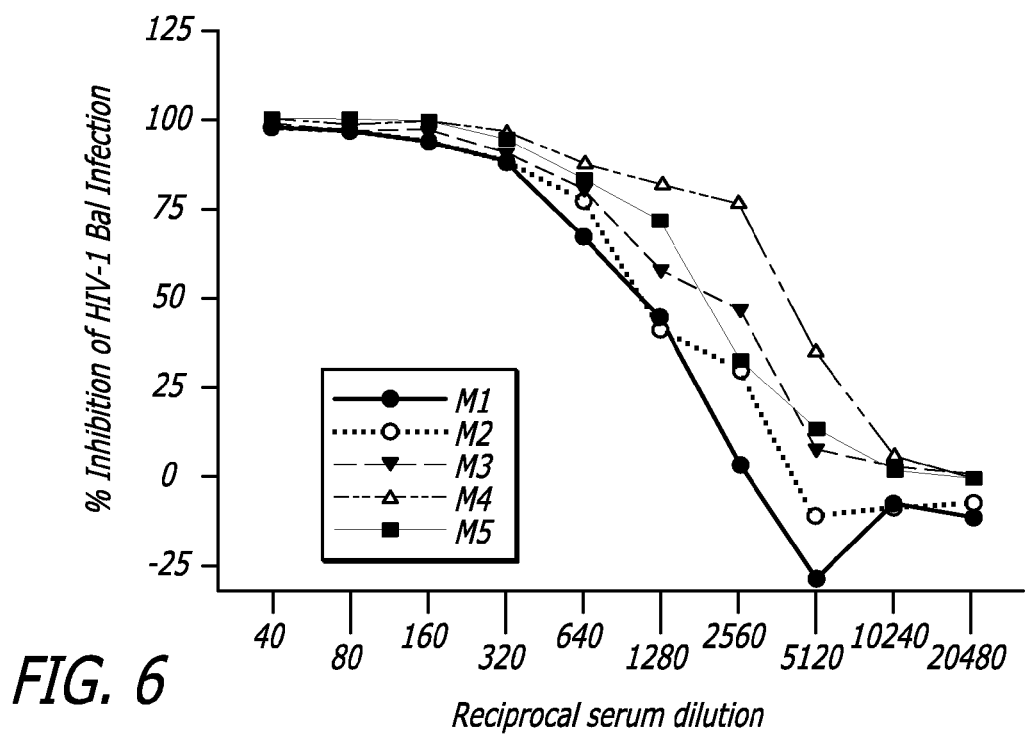
FIG. 6 depicts neutralization of HIV-1 Bal (R5) infection mediated by antisera against N46FdhFc.

These antisera were further tested for their neutralizing activity against infection by HIV-1 Bal (subtype B, R5) and an enfuvirtide-resistant HIV-1 strain NL4-3V38A/N42T in CEMx174 5.25M7 cells using luciferase assay by using a luciferase assay. Briefly, 50 µl of an antibody or antiserum from immunized mice at a series of dilution was incubated with an equal volume of an HIV-1 isolate at 0.01 multiplicity of infection (MOI) at 37° C. for 30 min, followed by addition of the mixture to 100 µl CEMx174 5.25M7 or TZM-bI cells ($1\times10^5$/ml) that were pre-cultured in a 96-well plate at 37° C. overnight. After further culture at 37° C. for 3 days, the cells were harvested and lysed with 50 µl lysing reagent. The luciferase activity was analyzed using a luciferase kit (Promega Corp.) and a luminometer (Model: Ultra 386, Tecan) according to the manufacture's instruction. The ND50 value of an antiserum was calculated using the software CalcuSyn. Similarly, anti-N46FdhFc antisera exhibited potent neutralizing activity against these two HIV-1 strains (FIG. 6 and Table 3).

The neutralizing activity of antibodies or antisera against primary HIV-1 isolates was determined as previously described in Jiang et al. (Antimicrob. Agents Chemother. 48, 4349-4359, 2004). Briefly, the peripheral blood mononuclear cells (PBMCs) were isolated from the blood of healthy donors using a standard density gradient (Histopaque-1077, Sigma) centrifugation. After incubation at 37° C. for 2 h, the nonadherent cells were collected and resuspended at $5\times10^5$/ml in RPMI 1640 medium containing 10% FBS, 5 µg of phytohemagglutinin (PHA)/ml, and 100 U of IL-2/ml, followed by incubation at 37° C. for 3 days. The PHA-stimulated cells were infected with the corresponding primary HIV-1 isolates at a multiplicity of infection (MOI) of 0.01 in the absence or presence of an antibody at a series of dilutions. The supernatants were collected 7 days post infection and mixed with equal volumes of 5% Triton X-100 for the detection of the p24 protein using ELISA as described in Jiang et al. with modification. Briefly, the wells of polystyrene plates (Immulon 1B, Dynex Technology, Chantilly, Va.) were coated with mouse anti-p24 mAb 183-12H-5C (NIH ARRRP) at 5 µg/ml in 0.05 M carbonate buffer (pH 9.6) at 4° C. overnight, followed by washes with PBS-T buffer (PBS containing 0.1% Tween-20) and blocking with PBS containing 2% dry fat-free milk (Bio-Rad Inc., Hercules, Calif.). Triton X-100 virus lysates were then added and incubated at 37° C. for 1 h. After extensive washes, human anti-p24 mAb (37G12, purchased from Polymun, Vienna, Austria), biotin labeled anti-human IgG1 (Santa Cruz Biotech., Santa Cruz, Calif.), SA-HRP and TMB were added sequentially. Reactions were terminated by addition of 1N $H_2SO_4$. Absorbance at 450 nm was recorded in an ELISA reader (Ultra 384, Tecan). Recombinant protein p24 (US Biological, Swampscott, Mass.) was used for establishing a standard dose response curve. These antisera against N46FdhFc also significantly neutralized infection of PBMCs by primary HIV-1 isolates 94UG103 (A, X4R5) and 92US657 (B, R5). However, the antisera directed against N46 and N46Fd at 1:40 dilution had no significant neutralizing activity against any of the viruses tested (Table 3). These results suggest that N46FdhFc is able to elicit antibodies with broad neutralizing activities.

TABLE 3

Neutralizing antibody titers of antisera directed against N46, N46Fd, and N46FdhFc

| HIV-1 | ND50 of antisera against | | |
|---|---|---|---|
| (subtype, tropism) | N46 | N46Fd | N46FdhFc |
| IIIB (B, X4)[1] | <40 | <40 | 663 |
| Bal (B, R5)[2] | <40 | <40 | 2314 |

TABLE 3-continued

Neutralizing antibody titers of antisera directed against N46, N46Fd, and N46FdhFc

| HIV-1 | ND50 of antisera against | | |
|---|---|---|---|
| (subtype, tropism) | N46 | N46Fd | N46FdhFc |
| NL43 V38A/N42T (B, R5)[2] | <40 | <40 | 732 |
| 94UG103 (A, X4R5)[3] | <40 | <40 | 265 |
| 92US657(B, R5)[3] | <40 | <40 | 142 |

[1]Neturalizing activity of the mouse antisera against infection by HIV-1 IIIB was tested in MT-2 cells by XTT assay;
[2]Neturalizing activity of the mouse antisera against infection by HIV-1 Bal and NL43 was tested in CEMx174 5.25M7 cells using luciferase assay;
[3]Neturalizing activity of the mouse antisera against infection by primary HIV-1 isolates 94UG103 and p2US657 was tested in PBMCs by p24 assay.

Example 6

Antibodies Induced by N46FdhFc Inhibited HIV-1-Mediated Cell-Cell Fusion

Figure 7:
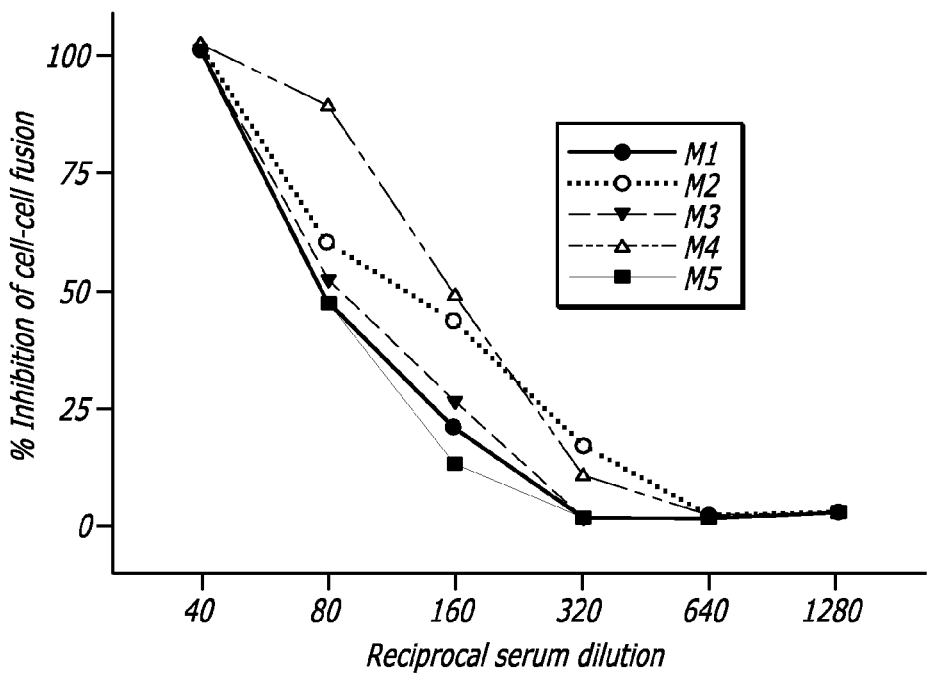
FIG. 7 depicts the inhibition of HIV-1-mediated cell-cell fusion mediated by antisera against N46FdhFc.

The HIV gp41 fusion intermediate (NHR-trimer) plays a critical role in the HIV-1 fusion process. Therefore, the antibodies induced against the gp41 NHR-trimer may have inhibitory activities on HIV-induced cell-cell fusion. The inhibitory activities of the antibodies or antisera on HIV-induced cell-cell fusion were determined using a dye transfer assay as described by Jiang et al. (Antimicrob. Agents Chemother. 48, 4349-4359, 2004). Briefly, H9/HIV-1$_{IIIB}$ cells were pre-labeled with a fluorescent dye, Calcein AM (Molecular Probes, Inc.), and incubated with a testing antibody or antiserum at a series of dilution at 37° C. for 30 min in a 96-well cell culture plate. Then the CD4+MT-2 cells were added to the H9/HIV-1IIIB cells at a ratio of 10:1, followed by incubation at 37° C. for 2 hrs. The fused and unfused calcein-labeled HIV-1-infected cells were counted under an inverted fluorescence microscope with an eyepiece micrometer disc. The percent inhibition of cell fusion by an antibody or antiserum and the EC50 values were calculated using the software CalcuSyn. Antisera from all the five mice immunized with N46FdhFc exhibited potent HIV-1 fusion inhibitory activity with average 1050 of 1:154 (FIG. 7), while the antisera from mice immunized with N46 and N46Fd exhibited no detectable inhibitory activity at 1:40.

Example 7

Antibodies Induced by N46FdhFc Bound Preferably to the gp41 Pocket Region

To determine the target site of the neutralizing antibodies elicited by the N46FdhFc, antibody titers in the anti-N46, anti-N46Fd and anti-N46FdhFc antisera was compared against a series of antigens, including N46, Fd, IQN17, and (ccIZN17)$_3$. For assessing the titers of antibodies in mouse sera against the gp41 NHR-trimer, the wells of a 96-well polystyrene plate (Costar) were coated with N46, Fd, or NHR-trimer, e.g., IQN17, or (ccIZN17)$_3$, at 10 µg/ml in 0.1 M Tris-HCl buffer (pH 8.8) at 4° C. overnight, and blocked with 2% non-fat milk in PBS for 3 hrs at 37° C. Mouse sera in a series of 2-fold dilution were added. The plate was washed with the washing buffer (PBS containing 0.01% Tween 20) for 6 times to remove any unbound antibodies. Horseradish peroxidase (HRP) linked goat-anti-mouse IgG was added, followed by incubation at 37° C. for 30 min. The reaction was visualized by addition of the substrate 3,3',5,5'-tetramethylbenzidine (TMB) and A450 was measured by using an ELISA reader (Tecan US).

As shown in Table 4, anti-N46 sera exhibited much higher binding titers against the N46 peptide and lower antibody titers against IQN17 and (ccIZN17)$_3$ than those directed against N46Fd and N46FdhFc. This suggests that anti-N46 antibodies mainly bind to linear epitopes in the NHR domain, while the antibodies to N46Fd and N46FdhFc preferably react with conformational epitopes in the NHR-trimers. Notably, antisera directed against N46FdhFc bound to IQN17 and (ccIZN17)$_3$ much more strongly than the anti-N46Fd antisera. This indicates that N46FdhFc elicits high levels of antibodies that may bind specifically to the pocket-forming sequence (N17), which overlaps the C-terminal fragment of N46 in the immunogen (FIG. 1), and that the neutralizing epitope(s) may be located in the pocket region. High titers of anti-Fd and anti-human IgG Fc antibodies were detected in the mouse antisera against N46FdhFc. However, the antisera from the mice immunized only with Fd or human IgG Fc had no virus neutralizing activity (data not shown), suggesting that the anti-Fd and anti-Fc antibodies in the anti-N46FdhFc sera are not responsible for the HIV-1 neutralization activity. Interestingly, the titer of antibodies to Fd in the anti-N46Fd sera (1:320,000) was much higher than that in the anti-N46FdhFc sera (1:12,126) (Table 4). This suggests that, although Fd in the fusion protein is highly immunogenic, the addition of the human IgG Fc to the C-terminus of N46Fd (FIG. 1) might suppress the immunogenicity of Fd. This may be one of the reasons why N46FdhFc, but not N46Fd, elicits neutralizing antibody responses. Apparently, fusion of the Fc domain of human IgG to the C-terminus of N46Fd is critical for the design of N46FdhFc as an immunogen. Firstly, the Fc domain in N46FdhFc may suppress the immunogenicity of Fd, perhaps by covering Fd (FIG. 1E) to prevent contact of Fd with antigen-presenting cells (APCs), and thus resulting in reduction of the immune interference of Fd with the immunogenicity of NHR-trimer. Secondly, the Fc domain in an immunogen may have an immunoenhancing effect because Fc-tagged protein can bind the Fc receptor (FcR) on dendritic cells or other APCs and thus promote internalization of the immunogen and major histocompatibility complex (MHC) class II-restricted antigen presentation. Thirdly, conjugation of a protein with Fc may prolong the half-life of the immunogen in immunized animals and thus enhance its immunogenicity.

TABLE 4

The titers of antisera binding to N46, Fd, and NHR-trimers.

| | Reciprocal of geometric mean titers of mouse antisera | | |
|---|---|---|---|
| Antigen | Anti-N46 | Anti-N46FD | Anti-N46FdhFc |
| N46 | 161,270 | 10,079 | 9,190 |
| Foldon | <100 | 320,000 | 12,126 |
| IQN17 | 22,449 | 35,919 | 211,121 |
| (ccIZN17)$_3$ | 17,818 | 17,959 | 320,000 |

Example 8

Antibodies Induced by N46FdhFc Blocked the gp41 Six-Helix Bundle Formation

To investigate the mechanism by which anti-N46FdhFc antibodies neutralize HIV-1 infection and block HIV-1-mediated cell-cell fusion, the inhibitory activities of antibodies in the mouse anti-N46, anti-N46Fd and anti-N46FdhFc antisera were compared with normal mouse IgG as control. The inhibitory activity of antibodies on the 6-HB core formation between N46 (SEQ ID NO. 3) and biotinylated C34 (C34-biotin) was determined by an ELISA with a conformation-specific monoclonal antibody (mAb) NC-1 (Jiang et al. J. Virol. 72, 10213-10217, 1998) and as previously described (He et al. Proc. Natl. Acad. Sci. USA 105, 16332-16337, 2008). Briefly, an antibody at a series of dilutions was pre-incubated with equal amount of N46 at 37° C. for 30 min, followed by addition of C34-biotin (0.5 µM). The mixture was added to the wells of a microplate coated with mAb NC-1 IgG (2 µg/ml in 0.1M Tris, pH 8.8) and blocked with 2% non-fat milk in PBS. The plate was then incubated for 30 min and washed with the washing buffer for 6 times to remove any unbound peptide. SA-HRP and TMB were added sequentially and A450 was measured. The percent inhibition of 6-HB formation and the $IC_{50}$ values were calculated.

Figure 8:
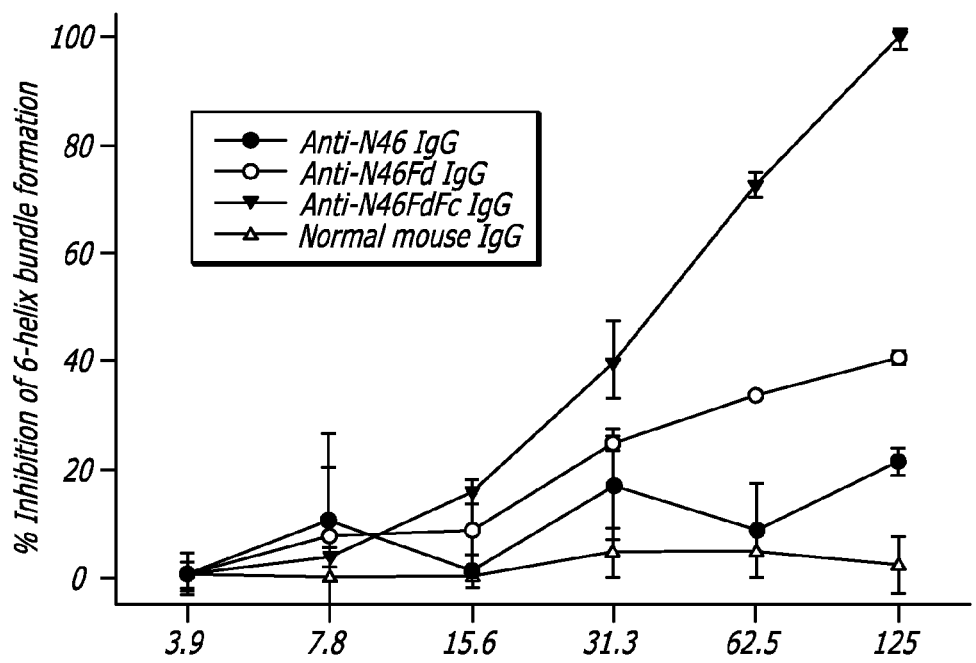
FIG. 8 depicts the inhibition of the gp41 six-helix bundle formation by IgG purified from antisera against N46FdhFc.

As shown in FIG. 8, anti-N46FdhFc IgG effectively blocked the 6-HB core formation between N46 and C34 as determined by ELISA. However, normal mouse IgG and antibodies specific for N46 and N46Fd had no significant effect on the inhibition of gp41 6-HB core formation. These results suggest that N46FdhFc elicits antibodies that bind preferably to the viral gp41 pocket region and thus block the fusion-active 6-HB core formation between the viral gp41 NHR and CHR, and consequently result in the inhibition of HIV-1 fusion with the target cell and viral entry.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An immunogenic composition for induction of an immune response against a lentivirus, said composition comprising a fusion protein, said fusion protein consisting of the following, in the order from the N-terminus to the C-terminus:
   a lentivirus gp41 N-terminal heptad repeat (NHR or HR1) region;
   a foldon trimerization motif; and
   an immunoenhancer sequence.

2. The immunogenic composition of claim 1 wherein the lentivirus is selected from the group consisting of HIV-1, HIV-2, and SIV.

3. The immunogenic composition of claim 1 wherein the immunoenhancer is selected from the group consisting of the Fc domain of immunoglobulin G, complement component C3d, and Onchocerca volvulus activation associated protein-1 (Ov-ASP-1).

4. The immunogenic composition of claim 3 wherein the Fc domain of immunoglobulin G or complement component C3d is from a mammal selected from the group consisting of mouse, rabbit, pig, non-human primate, and human.

5. The immunogenic composition of claim 1 wherein the composition further comprises an adjuvant.

6. An immunogenic composition for induction of an immune response against a lentivirus, said composition comprising a fusion protein, said fusion protein consisting of:
   (a) the following, in the order from the N-terminus to the C-terminus:
      a lentivirus gp41 N-terminal heptad repeat (NHR or HR1) region,
      a foldon trimerization motif, and
      an immunoenhancer sequence; and
   (b) a His tag or a GST sequence at either the N-terminus or the C-terminus.

7. A method of inducing an immune response to HIV comprising the steps of
   administering the immunogenic composition of claim 1 to a mammal in need thereof; and
   inducing an immune response in said mammal to said HIV.

8. The method of claim 7 wherein said immunogenic composition is administered by a route selected from the group consisting of subcutaneous, intramuscular, intraperitoneal, and mucous immunization.

9. The method of claim 7 wherein said immune response results in the production of neutralizing antibodies against HIV in said mammal.

10. An immunogenic composition for induction of an immune response against a lentivirus, said composition comprising a fusion protein, said fusion protein consisting of the following, in the order from the N-terminus to the C-terminus:
    an N46 sequence of human immunodeficiency virus gp41;
    a foldon trimerization motif; and
    a human immunoglobulin G Fc sequence.

11. The immunogenic composition of claim 6 wherein the lentivirus is selected from the group consisting of HIV-1, HIV-2, and SIV.

12. The immunogenic composition of claim 6 wherein the immunoenhancer is selected from the group consisting of the Fc domain of immunoglobulin G, complement component C3d, and Onchocerca volvulus activation associated protein-1 (Ov-ASP-1).

13. The immunogenic composition of claim 12 wherein the Fc domain of immunoglobulin G or complement component C3d is from a mammal selected from the group consisting of mouse, rabbit, pig, non-human primate, and human.

14. The immunogenic composition of claim 6 wherein the composition further comprises an adjuvant.

15. The method of claim 7 wherein the immunogenic composition is administered in combination with an adjuvant.

* * * * *

SEQUENCE LISTING

<160> NUMBER OF SEQ ID NOS: 36

<210> SEQ ID NO 1
<211> LENGTH: 856
<212> TYPE: PRT

<213> ORGANISM: Human immunodeficiency virus type 1

<400> SEQUENCE: 1

```
Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
                35                  40                  45

Thr Thr Thr Leu Phe Cys Ala Ser Asp Ala Lys Ala Tyr Asp Thr Glu
            50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
                115                 120                 125

Leu Lys Cys Thr Asp Leu Lys Asn Asp Thr Asn Thr Asn Ser Ser Ser
            130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
                195                 200                 205

Ser Phe Glu Pro Ile Pro Ile His Tyr Cys Ala Pro Ala Gly Phe Ala
            210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Val Val Ile
            260                 265                 270

Arg Ser Val Asn Phe Thr Asp Asn Ala Lys Thr Ile Ile Val Gln Leu
                275                 280                 285

Asn Thr Ser Val Glu Ile Asn Cys Thr Arg Pro Asn Asn Thr Arg
            290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
            340                 345                 350

Phe Gly Asn Asn Lys Thr Ile Ile Phe Lys Gln Ser Ser Gly Gly Asp
                355                 360                 365

Pro Glu Ile Val Thr His Ser Phe Asn Cys Gly Gly Glu Phe Phe Tyr
            370                 375                 380

Cys Asn Ser Thr Gln Leu Phe Asn Ser Thr Trp Phe Asn Ser Thr Trp
385                 390                 395                 400
```

-continued

```
Ser Thr Glu Gly Ser Asn Asn Thr Glu Gly Ser Asp Thr Ile Thr Leu
                405                 410                 415
Pro Cys Arg Ile Lys Gln Ile Ile Asn Met Trp Gln Lys Val Gly Lys
            420                 425                 430
Ala Met Tyr Ala Pro Pro Ile Ser Gly Gln Ile Arg Cys Ser Ser Asn
        435                 440                 445
Ile Thr Gly Leu Leu Leu Thr Arg Asp Gly Gly Asn Ser Asn Asn Glu
    450                 455                 460
Ser Glu Ile Phe Arg Pro Gly Gly Gly Asp Met Arg Asp Asn Trp Arg
465                 470                 475                 480
Ser Glu Leu Tyr Lys Tyr Lys Val Val Lys Ile Glu Pro Leu Gly Val
                485                 490                 495
Ala Pro Thr Lys Ala Lys Arg Arg Val Val Gln Arg Glu Lys Arg Ala
            500                 505                 510
Val Gly Ile Gly Ala Leu Phe Leu Gly Phe Leu Gly Ala Ala Gly Ser
        515                 520                 525
Thr Met Gly Ala Ala Ser Met Thr Leu Thr Val Gln Ala Arg Gln Leu
    530                 535                 540
Leu Ser Gly Ile Val Gln Gln Gln Asn Asn Leu Leu Arg Ala Ile Glu
545                 550                 555                 560
Ala Gln Gln His Leu Leu Gln Leu Thr Val Trp Gly Ile Lys Gln Leu
                565                 570                 575
Gln Ala Arg Ile Leu Ala Val Glu Arg Tyr Leu Lys Asp Gln Gln Leu
            580                 585                 590
Leu Gly Ile Trp Gly Cys Ser Gly Lys Leu Ile Cys Thr Thr Ala Val
        595                 600                 605
Pro Trp Asn Ala Ser Trp Ser Asn Lys Ser Leu Glu Gln Ile Trp Asn
    610                 615                 620
His Thr Thr Trp Met Glu Trp Asp Arg Glu Ile Asn Asn Tyr Thr Ser
625                 630                 635                 640
Leu Ile His Ser Leu Ile Glu Glu Ser Gln Asn Gln Gln Glu Lys Asn
                645                 650                 655
Glu Gln Glu Leu Leu Glu Leu Asp Lys Trp Ala Ser Leu Trp Asn Trp
            660                 665                 670
Phe Asn Ile Thr Asn Trp Leu Trp Tyr Ile Lys Leu Phe Ile Met Ile
        675                 680                 685
Val Gly Gly Leu Val Gly Leu Arg Ile Val Phe Ala Val Leu Ser Ile
    690                 695                 700
Val Asn Arg Val Arg Gln Gly Tyr Ser Pro Leu Ser Phe Gln Thr His
705                 710                 715                 720
Leu Pro Thr Pro Arg Gly Pro Asp Arg Pro Glu Gly Ile Glu Glu Glu
                725                 730                 735
Gly Gly Glu Arg Asp Arg Asp Arg Ser Ile Arg Leu Val Asn Gly Ser
            740                 745                 750
Leu Ala Leu Ile Trp Asp Asp Leu Arg Ser Leu Cys Leu Phe Ser Tyr
        755                 760                 765
His Arg Leu Arg Asp Leu Leu Leu Ile Val Thr Arg Ile Val Glu Leu
    770                 775                 780
Leu Gly Arg Arg Gly Trp Glu Ala Leu Lys Tyr Trp Trp Asn Leu Leu
785                 790                 795                 800
Gln Tyr Trp Ser Gln Glu Leu Lys Asn Ser Ala Val Ser Leu Leu Asn
                805                 810                 815
Ala Thr Ala Ile Ala Val Ala Glu Gly Thr Asp Arg Val Ile Glu Val
```

```
            820                 825                 830
Val Gln Gly Ala Cys Arg Ala Ile Arg His Ile Pro Arg Arg Ile Arg
                835                 840                 845

Gln Gly Leu Glu Arg Ile Leu Leu
    850                 855

<210> SEQ ID NO 2
<211> LENGTH: 345
<212> TYPE: PRT
<213> ORGANISM: Human immunodeficiency virus type 1

<400> SEQUENCE: 2

Ala Val Gly Ile Gly Ala Leu Phe Leu Gly Phe Leu Gly Ala Ala Gly
1               5                   10                  15

Ser Thr Met Gly Ala Ala Ser Met Thr Leu Thr Val Gln Ala Arg Gln
            20                  25                  30

Leu Leu Ser Gly Ile Val Gln Gln Gln Asn Asn Leu Leu Arg Ala Ile
        35                  40                  45

Glu Ala Gln Gln His Leu Leu Gln Leu Thr Val Trp Gly Ile Lys Gln
    50                  55                  60

Leu Gln Ala Arg Ile Leu Ala Val Glu Arg Tyr Leu Lys Asp Gln Gln
65                  70                  75                  80

Leu Leu Gly Ile Trp Gly Cys Ser Gly Lys Leu Ile Cys Thr Thr Ala
                85                  90                  95

Val Pro Trp Asn Ala Ser Trp Ser Asn Lys Ser Leu Glu Gln Ile Trp
            100                 105                 110

Asn His Thr Thr Trp Met Glu Trp Asp Arg Glu Ile Asn Asn Tyr Thr
        115                 120                 125

Ser Leu Ile His Ser Leu Ile Glu Glu Ser Gln Asn Gln Gln Glu Lys
    130                 135                 140

Asn Glu Gln Glu Leu Leu Glu Leu Asp Lys Trp Ala Ser Leu Trp Asn
145                 150                 155                 160

Trp Phe Asn Ile Thr Asn Trp Leu Trp Tyr Ile Lys Leu Phe Ile Met
                165                 170                 175

Ile Val Gly Gly Leu Val Gly Leu Arg Ile Val Phe Ala Val Leu Ser
            180                 185                 190

Ile Val Asn Arg Val Arg Gln Gly Tyr Ser Pro Leu Ser Phe Gln Thr
        195                 200                 205

His Leu Pro Thr Pro Arg Gly Pro Asp Arg Pro Glu Gly Ile Glu Glu
    210                 215                 220

Glu Gly Gly Glu Arg Asp Arg Asp Arg Ser Ile Arg Leu Val Asn Gly
225                 230                 235                 240

Ser Leu Ala Leu Ile Trp Asp Asp Leu Arg Ser Leu Cys Leu Phe Ser
                245                 250                 255

Tyr His Arg Leu Arg Asp Leu Leu Leu Ile Val Thr Arg Ile Val Glu
            260                 265                 270

Leu Leu Gly Arg Arg Gly Trp Glu Ala Leu Lys Tyr Trp Trp Asn Leu
        275                 280                 285

Leu Gln Tyr Trp Ser Gln Glu Leu Lys Asn Ser Ala Val Ser Leu Leu
    290                 295                 300

Asn Ala Thr Ala Ile Ala Val Ala Glu Gly Thr Asp Arg Val Ile Glu
305                 310                 315                 320

Val Val Gln Gly Ala Cys Arg Ala Ile Arg His Ile Pro Arg Arg Ile
                325                 330                 335
```

-continued

Arg Gln Gly Leu Glu Arg Ile Leu Leu
            340                 345

<210> SEQ ID NO 3
<211> LENGTH: 45
<212> TYPE: PRT
<213> ORGANISM: Human immunodeficiency virus type 1

<400> SEQUENCE: 3

Thr Leu Thr Val Gln Ala Arg Gln Leu Leu Ser Gly Ile Val Gln Gln
1               5                   10                  15

Gln Asn Asn Leu Leu Arg Ala Ile Glu Ala Gln Gln His Leu Leu Gln
            20                  25                  30

Leu Thr Val Trp Gly Ile Lys Gln Leu Gln Ala Arg Ile
        35                  40                  45

<210> SEQ ID NO 4
<211> LENGTH: 46
<212> TYPE: PRT
<213> ORGANISM: Human immunodeficiency virus type 1

<400> SEQUENCE: 4

Thr Leu Thr Val Gln Ala Arg Gln Leu Leu Ser Gly Ile Val Gln Gln
1               5                   10                  15

Gln Ser Asn Leu Leu Arg Ala Ile Glu Ala Gln Gln His Leu Leu Lys
            20                  25                  30

Leu Thr Val Trp Gly Ile Lys Gln Leu Gln Ala Arg Val Leu
        35                  40                  45

<210> SEQ ID NO 5
<211> LENGTH: 46
<212> TYPE: PRT
<213> ORGANISM: Human immunodeficiency virus type 1

<400> SEQUENCE: 5

Thr Leu Thr Val Gln Ala Arg Gln Leu Leu Ser Gly Ile Val Gln Gln
1               5                   10                  15

Gln Ser Asn Leu Leu Arg Ala Ile Glu Ala Gln Gln His Leu Leu Gln
            20                  25                  30

Leu Thr Val Trp Gly Ile Lys Gln Leu Gln Ala Arg Val Leu
        35                  40                  45

<210> SEQ ID NO 6
<211> LENGTH: 46
<212> TYPE: PRT
<213> ORGANISM: Human immunodeficiency virus type 1

<400> SEQUENCE: 6

Thr Leu Thr Ala Gln Ala Arg Gln Leu Leu Ser Gly Ile Val Gln Gln
1               5                   10                  15

Gln Ser Asn Leu Leu Arg Ala Ile Glu Ala Gln Gln His Leu Leu Gln
            20                  25                  30

Leu Thr Val Trp Gly Ile Lys Gln Leu Gln Thr Arg Val Leu
        35                  40                  45

<210> SEQ ID NO 7
<211> LENGTH: 46
<212> TYPE: PRT
<213> ORGANISM: Human immunodeficiency virus type 1

<400> SEQUENCE: 7

```
Thr Leu Thr Val Gln Ala Arg Gln Leu Leu Ser Gly Ile Val Gln His
1               5                   10                  15

Gln Asn Asn Leu Leu Met Ala Ile Glu Ala Gln Gln His Leu Leu Gln
            20                  25                  30

Leu Thr Val Trp Gly Ile Lys Gln Leu Gln Ala Arg Ile Leu
        35                  40                  45
```

<210> SEQ ID NO 8
<211> LENGTH: 45
<212> TYPE: PRT
<213> ORGANISM: Human immunodeficiency virus type 1

<400> SEQUENCE: 8

```
Thr Leu Thr Val Gln Ala Arg Gln Leu Leu Gly Ile Val Gln Gln Gln
1               5                   10                  15

Ser Asn Leu Leu Arg Ala Ile Glu Ala Gln Gln His Leu Leu Gln Leu
            20                  25                  30

Thr Val Trp Gly Ile Lys Gln Leu Gln Ala Arg Val Leu
        35                  40                  45
```

<210> SEQ ID NO 9
<211> LENGTH: 46
<212> TYPE: PRT
<213> ORGANISM: Human immunodeficiency virus type 1

<400> SEQUENCE: 9

```
Thr Leu Thr Val Gln Ala Arg Gln Leu Leu Ser Gly Ile Val Gln Gln
1               5                   10                  15

Gln Ser Asn Leu Leu Arg Ala Ile Glu Ala Gln Gln His Leu Leu Gln
            20                  25                  30

Leu Thr Val Trp Gly Ile Lys Gln Leu Gln Ala Arg Val Leu
        35                  40                  45
```

<210> SEQ ID NO 10
<211> LENGTH: 46
<212> TYPE: PRT
<213> ORGANISM: Human immunodeficiency virus type 1

<400> SEQUENCE: 10

```
Thr Leu Thr Val Gln Val Lys Lys Leu Leu Phe Gly Ile Val Gln Gln
1               5                   10                  15

Gln Ser Asn Leu Leu Arg Ala Ile Glu Ala Gln Gln His Leu Leu Gln
            20                  25                  30

Leu Thr Val Trp Gly Ile Lys Gln Leu Gln Ala Arg Val Leu
        35                  40                  45
```

<210> SEQ ID NO 11
<211> LENGTH: 46
<212> TYPE: PRT
<213> ORGANISM: Human immunodeficiency virus type 1

<400> SEQUENCE: 11

```
Ala Leu Thr Val Arg Thr His Thr Leu Ile Lys Gly Ile Val Gln Gln
1               5                   10                  15

Gln Asp Asn Leu Leu Arg Ala Ile Gln Ala Gln Gln Leu Leu Arg
            20                  25                  30

Leu Ser Val Trp Gly Ile Arg Gln Leu Arg Ala Arg Leu Leu
        35                  40                  45
```

<210> SEQ ID NO 12

```
<211> LENGTH: 46
<212> TYPE: PRT
<213> ORGANISM: Human immunodeficiency virus type 2

<400> SEQUENCE: 12

Thr Leu Ser Ala Gln Ser Arg Thr Leu Leu Ala Gly Ile Val Gln Gln
1               5                   10                  15

Gln Gln Gln Leu Leu Asp Val Val Lys Arg Gln Gln Glu Met Leu Arg
                20                  25                  30

Leu Thr Val Trp Gly Thr Lys Asn Leu Gln Ala Arg Val Thr
            35                  40                  45

<210> SEQ ID NO 13
<211> LENGTH: 17
<212> TYPE: PRT
<213> ORGANISM: Human immunodeficiency virus type 1

<400> SEQUENCE: 13

Leu Leu Gln Leu Thr Val Trp Gly Ile Lys Gln Leu Gln Ala Arg Ile
1               5                   10                  15

Leu

<210> SEQ ID NO 14
<211> LENGTH: 27
<212> TYPE: PRT
<213> ORGANISM: Human immunodeficiency virus type 1

<400> SEQUENCE: 14

Glu Ala Gln Gln His Leu Leu Gln Leu Thr Val Trp Gly Ile Lys Gln
1               5                   10                  15

Leu Gln Ala Arg Ile Leu Ala Val Glu Arg Tyr
                20                  25

<210> SEQ ID NO 15
<211> LENGTH: 36
<212> TYPE: PRT
<213> ORGANISM: Human immunodeficiency virus type 1

<400> SEQUENCE: 15

Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Leu Gln
                20                  25                  30

Ala Arg Ile Leu
            35

<210> SEQ ID NO 16
<211> LENGTH: 51
<212> TYPE: PRT
<213> ORGANISM: Human immunodeficiency virus type 1

<400> SEQUENCE: 16

Gln Ala Arg Gln Leu Leu Ser Gly Ile Val Gln Gln Gln Asn Asn Leu
1               5                   10                  15

Leu Arg Ala Ile Glu Ala Gln Gln His Leu Leu Gln Leu Thr Val Trp
                20                  25                  30

Gly Ile Lys Gln Leu Gln Ala Arg Ile Leu Ala Val Glu Arg Tyr Leu
            35                  40                  45

Lys Gln Gln
    50
```

<210> SEQ ID NO 17
<211> LENGTH: 63
<212> TYPE: PRT
<213> ORGANISM: Human immunodeficiency virus type 1

<400> SEQUENCE: 17

```
Ser Thr Met Gly Ala Ala Ser Met Thr Leu Thr Val Gln Ala Arg Gln
1               5                   10                  15

Leu Leu Ser Gly Ile Val Gln Gln Asn Asn Leu Leu Arg Ala Ile
            20                  25                  30

Glu Ala Gln Gln His Leu Leu Gln Leu Thr Val Trp Gly Ile Lys Gln
        35                  40                  45

Leu Gln Ala Arg Ile Leu Ala Val Glu Arg Tyr Leu Lys Asp Gln
    50                  55                  60
```

<210> SEQ ID NO 18
<211> LENGTH: 27
<212> TYPE: PRT
<213> ORGANISM: Bacteriophage T4

<400> SEQUENCE: 18

```
Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25
```

<210> SEQ ID NO 19
<211> LENGTH: 28
<212> TYPE: PRT
<213> ORGANISM: Human immunodeficiency virus

<400> SEQUENCE: 19

```
Arg Met Lys Gln Ile Glu Asp Lys Ile Glu Glu Ile Glu Ser Lys Gln
1               5                   10                  15

Lys Lys Ile Glu Asn Glu Ile Ala Arg Ile Lys Lys
            20                  25
```

<210> SEQ ID NO 20
<211> LENGTH: 26
<212> TYPE: PRT
<213> ORGANISM: Human immunodeficiency virus

<400> SEQUENCE: 20

```
Ile Lys Lys Glu Ile Glu Ala Ile Lys Lys Glu Gln Glu Ala Ile Lys
1               5                   10                  15

Lys Lys Ile Glu Ala Ile Glu Lys Glu Ile
            20                  25
```

<210> SEQ ID NO 21
<211> LENGTH: 229
<212> TYPE: PRT
<213> ORGANISM: Homo sapiens

<400> SEQUENCE: 21

```
Arg Ser Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45
```

```
Ser His Glu Asp Pro Glu Val Lys Phe Asn Trp Tyr Val Asp Gly Val
 50                  55                  60

Glu Val His Asn Ala Lys Thr Lys Pro Arg Glu Glu Gln Tyr Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
        115                 120                 125

Gln Val Tyr Thr Leu Pro Pro Ser Arg Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Gly Leu His Asn His Tyr Thr Gln Lys Ser Leu Ser
210                 215                 220

Leu Ser Pro Gly Lys
225

<210> SEQ ID NO 22
<211> LENGTH: 234
<212> TYPE: PRT
<213> ORGANISM: Mus sp.

<400> SEQUENCE: 22

Arg Ser Pro Arg Gly Pro Thr Ile Lys Pro Cys Pro Pro Cys Lys Cys
 1               5                  10                  15

Pro Ala Pro Asn Leu Leu Gly Gly Pro Ser Val Phe Ile Phe Pro Pro
             20                  25                  30

Lys Ile Lys Asp Val Leu Met Ile Ser Leu Ser Pro Ile Val Thr Cys
         35                  40                  45

Val Val Val Asp Val Ser Glu Asp Asp Pro Asp Val Gln Ile Ser Trp
 50                  55                  60

Phe Val Asn Asn Val Glu Val His Thr Ala Gln Thr Gln Thr His Arg
 65                  70                  75                  80

Glu Asp Tyr Asn Ser Thr Leu Arg Val Val Ser Ala Leu Pro Ile Gln
                 85                  90                  95

His Gln Asp Trp Met Ser Gly Lys Glu Phe Lys Cys Lys Val Asn Asn
            100                 105                 110

Lys Asp Leu Pro Ala Pro Ile Glu Arg Thr Ile Ser Lys Pro Lys Gly
        115                 120                 125

Ser Val Arg Ala Pro Gln Val Tyr Val Leu Pro Pro Pro Glu Glu Glu
130                 135                 140

Met Thr Lys Lys Gln Val Thr Leu Thr Cys Met Val Thr Asp Phe Met
145                 150                 155                 160

Pro Glu Asp Ile Tyr Val Glu Trp Thr Asn Asn Gly Lys Thr Glu Leu
                165                 170                 175

Asn Tyr Lys Asn Thr Glu Pro Val Leu Asp Ser Asp Gly Ser Tyr Phe
            180                 185                 190
```

Met Tyr Ser Lys Leu Arg Val Glu Lys Lys Asn Trp Val Glu Arg Asn
              195                 200                 205

Ser Tyr Ser Cys Ser Val Val His Glu Gly Leu His Asn His His Thr
              210                 215                 220

Thr Lys Ser Phe Ser Arg Thr Pro Gly Lys
225                 230

<210> SEQ ID NO 23
<211> LENGTH: 225
<212> TYPE: PRT
<213> ORGANISM: Oryctolagus cuniculus

<400> SEQUENCE: 23

Arg Ser Ser Lys Pro Thr Cys Pro Pro Pro Glu Leu Leu Gly Gly Pro
1               5                   10                  15

Ser Val Phe Ile Phe Pro Pro Lys Pro Lys Asp Thr Leu Met Ile Ser
              20                  25                  30

Arg Thr Pro Glu Val Thr Cys Val Val Val Asp Val Ser Gln Asp Asp
          35                  40                  45

Pro Glu Val Gln Phe Thr Trp Tyr Ile Asn Asn Glu Gln Val Arg Thr
    50                  55                  60

Ala Arg Pro Pro Leu Arg Glu Gln Gln Phe Asn Ser Thr Ile Arg Val
65                  70                  75                  80

Val Ser Thr Leu Pro Ile Ala His Gln Asp Trp Leu Arg Gly Lys Glu
                85                  90                  95

Phe Lys Cys Lys Val His Asn Lys Ala Leu Pro Ala Pro Ile Glu Lys
            100                 105                 110

Thr Ile Ser Lys Ala Arg Gly Gln Pro Leu Glu Pro Lys Val Tyr Thr
        115                 120                 125

Met Gly Pro Pro Arg Glu Glu Leu Ser Ser Arg Ser Val Ser Leu Thr
    130                 135                 140

Cys Met Ile Asn Gly Phe Tyr Pro Ser Asp Ile Ser Val Glu Trp Glu
145                 150                 155                 160

Lys Asn Gly Lys Ala Glu Asp Asn Tyr Lys Thr Thr Pro Ala Val Leu
                165                 170                 175

Asp Ser Asp Gly Ser Tyr Phe Leu Tyr Ser Lys Leu Ser Val Pro Thr
            180                 185                 190

Ser Glu Trp Gln Arg Gly Asp Val Phe Thr Cys Ser Val Met His Glu
        195                 200                 205

Ala Leu His Asn His Tyr Thr Gln Lys Ser Ile Ser Arg Ser Pro Gly
    210                 215                 220

Lys
225

<210> SEQ ID NO 24
<211> LENGTH: 73
<212> TYPE: PRT
<213> ORGANISM: Artificial
<220> FEATURE:
<223> OTHER INFORMATION: N46Fd fusion protein comprising N46 fragment
      of gp41 and foldon sequnce

<400> SEQUENCE: 24

Thr Leu Thr Val Gln Ala Arg Gln Leu Leu Ser Gly Ile Val Gln Gln
1               5                   10                  15

Gln Asn Asn Leu Leu Arg Ala Ile Glu Ala Gln Gln His Leu Leu Gln
              20                  25                  30

Leu Thr Val Trp Gly Ile Lys Gln Leu Gln Ala Arg Ile Leu Gly Tyr
        35                  40                  45

Ile Pro Glu Ala Pro Arg Asp Gly Gln Ala Tyr Val Arg Lys Asp Gly
 50                  55                  60

Glu Trp Val Leu Leu Ser Thr Phe Leu
 65                  70

<210> SEQ ID NO 25
<211> LENGTH: 275
<212> TYPE: PRT
<213> ORGANISM: Artificial
<220> FEATURE:
<223> OTHER INFORMATION: N46hFc fusion protein comprising the N46
      fragment of gp41 and human Fc

<400> SEQUENCE: 25

Thr Leu Thr Val Gln Ala Arg Gln Leu Leu Ser Gly Ile Val Gln Gln
 1               5                   10                  15

Gln Asn Asn Leu Leu Arg Ala Ile Glu Ala Gln Gln His Leu Leu Gln
            20                  25                  30

Leu Thr Val Trp Gly Ile Lys Gln Leu Gln Ala Arg Ile Leu Arg Ser
        35                  40                  45

Asp Lys Thr His Thr Cys Pro Pro Cys Pro Ala Pro Glu Leu Leu Gly
 50                  55                  60

Gly Pro Ser Val Phe Leu Phe Pro Pro Lys Pro Lys Asp Thr Leu Met
 65                  70                  75                  80

Ile Ser Arg Thr Pro Glu Val Thr Cys Val Val Val Asp Val Ser His
                85                  90                  95

Glu Asp Pro Glu Val Lys Phe Asn Trp Tyr Val Asp Gly Val Glu Val
            100                 105                 110

His Asn Ala Lys Thr Lys Pro Arg Glu Glu Gln Tyr Asn Ser Thr Tyr
        115                 120                 125

Arg Val Val Ser Val Leu Thr Val Leu His Gln Asp Trp Leu Asn Gly
    130                 135                 140

Lys Glu Tyr Lys Cys Lys Val Ser Asn Lys Ala Leu Pro Ala Pro Ile
145                 150                 155                 160

Glu Lys Thr Ile Ser Lys Ala Lys Gly Gln Pro Arg Glu Pro Gln Val
                165                 170                 175

Tyr Thr Leu Pro Pro Ser Arg Glu Glu Met Thr Lys Asn Gln Val Ser
            180                 185                 190

Leu Thr Cys Leu Val Lys Gly Phe Tyr Pro Ser Asp Ile Ala Val Glu
        195                 200                 205

Trp Glu Ser Asn Gly Gln Pro Glu Asn Asn Tyr Lys Thr Thr Pro Pro
    210                 215                 220

Val Leu Asp Ser Asp Gly Ser Phe Phe Leu Tyr Ser Lys Leu Thr Val
225                 230                 235                 240

Asp Lys Ser Arg Trp Gln Gln Gly Asn Val Phe Ser Cys Ser Val Met
                245                 250                 255

His Glu Gly Leu His Asn His Tyr Thr Gln Lys Ser Leu Ser Leu Ser
            260                 265                 270

Pro Gly Lys
        275

<210> SEQ ID NO 26
<211> LENGTH: 302
<212> TYPE: PRT

<213> ORGANISM: Artificial
<220> FEATURE:
<223> OTHER INFORMATION: N46FdhFc fusion protein comprising the N46
      fragment of gp41, foldon sequence and human Fc

<400> SEQUENCE: 26

```
Thr Leu Thr Val Gln Ala Arg Gln Leu Leu Ser Gly Ile Val Gln Gln
1               5                   10                  15

Gln Asn Asn Leu Leu Arg Ala Ile Glu Ala Gln Gln His Leu Leu Gln
            20                  25                  30

Leu Thr Val Trp Gly Ile Lys Gln Leu Gln Ala Arg Ile Leu Gly Tyr
        35                  40                  45

Ile Pro Glu Ala Pro Arg Asp Gly Gln Ala Tyr Val Arg Lys Asp Gly
50                  55                  60

Glu Trp Val Leu Leu Ser Thr Phe Leu Arg Ser Asp Lys Thr His Thr
65                  70                  75                  80

Cys Pro Pro Cys Pro Ala Pro Glu Leu Leu Gly Gly Pro Ser Val Phe
                85                  90                  95

Leu Phe Pro Pro Lys Pro Lys Asp Thr Leu Met Ile Ser Arg Thr Pro
            100                 105                 110

Glu Val Thr Cys Val Val Val Asp Val Ser His Glu Asp Pro Glu Val
        115                 120                 125

Lys Phe Asn Trp Tyr Val Asp Gly Val Glu Val His Asn Ala Lys Thr
130                 135                 140

Lys Pro Arg Glu Glu Gln Tyr Asn Ser Thr Tyr Arg Val Val Ser Val
145                 150                 155                 160

Leu Thr Val Leu His Gln Asp Trp Leu Asn Gly Lys Glu Tyr Lys Cys
                165                 170                 175

Lys Val Ser Asn Lys Ala Leu Pro Ala Pro Ile Glu Lys Thr Ile Ser
            180                 185                 190

Lys Ala Lys Gly Gln Pro Arg Glu Pro Gln Val Tyr Thr Leu Pro Pro
        195                 200                 205

Ser Arg Glu Glu Met Thr Lys Asn Gln Val Ser Leu Thr Cys Leu Val
210                 215                 220

Lys Gly Phe Tyr Pro Ser Asp Ile Ala Val Glu Trp Glu Ser Asn Gly
225                 230                 235                 240

Gln Pro Glu Asn Asn Tyr Lys Thr Thr Pro Pro Val Leu Asp Ser Asp
                245                 250                 255

Gly Ser Phe Phe Leu Tyr Ser Lys Leu Thr Val Asp Lys Ser Arg Trp
            260                 265                 270

Gln Gln Gly Asn Val Phe Ser Cys Ser Val Met His Glu Gly Leu His
        275                 280                 285

Asn His Tyr Thr Gln Lys Ser Leu Ser Leu Ser Pro Gly Lys
290                 295                 300
```

<210> SEQ ID NO 27
<211> LENGTH: 302
<212> TYPE: PRT
<213> ORGANISM: Artificial
<220> FEATURE:
<223> OTHER INFORMATION: N46FdmFc comprising the N46 fragment of gp41,
      foldon sequence and murine Fc

<400> SEQUENCE: 27

```
Thr Leu Thr Val Gln Ala Arg Gln Leu Leu Ser Gly Ile Val Gln Gln
1               5                   10                  15

Gln Asn Asn Leu Leu Arg Ala Ile Glu Ala Gln Gln His Leu Leu Gln
            20
```

```
            20                  25                  30
Leu Thr Val Trp Gly Ile Lys Gln Leu Gln Ala Arg Ile Leu Gly Tyr
            35                  40                  45

Ile Pro Glu Ala Pro Arg Asp Gly Gln Ala Tyr Val Arg Lys Asp Gly
        50                  55                  60

Glu Trp Val Leu Leu Ser Thr Phe Leu Arg Ser Asp Lys Thr His Thr
65                  70                  75                  80

Cys Pro Pro Cys Pro Ala Pro Glu Leu Leu Gly Gly Pro Ser Val Phe
                85                  90                  95

Leu Phe Pro Pro Lys Pro Lys Asp Thr Leu Met Ile Ser Arg Thr Pro
            100                 105                 110

Glu Val Thr Cys Val Val Val Asp Val Ser His Glu Asp Pro Glu Val
            115                 120                 125

Lys Phe Asn Trp Tyr Val Asp Gly Val Glu Val His Asn Ala Lys Thr
        130                 135                 140

Lys Pro Arg Glu Glu Gln Tyr Asn Ser Thr Tyr Arg Val Val Ser Val
145                 150                 155                 160

Leu Thr Val Leu His Gln Asp Trp Leu Asn Gly Lys Glu Tyr Lys Cys
                165                 170                 175

Lys Val Ser Asn Lys Ala Leu Pro Ala Pro Ile Glu Lys Thr Ile Ser
            180                 185                 190

Lys Ala Lys Gly Gln Pro Arg Glu Pro Gln Val Tyr Thr Leu Pro Pro
            195                 200                 205

Ser Arg Glu Glu Met Thr Lys Asn Gln Val Ser Leu Thr Cys Leu Val
        210                 215                 220

Lys Gly Phe Tyr Pro Ser Asp Ile Ala Val Glu Trp Glu Ser Asn Gly
225                 230                 235                 240

Gln Pro Glu Asn Asn Tyr Lys Thr Thr Pro Pro Val Leu Asp Ser Asp
                245                 250                 255

Gly Ser Phe Phe Leu Tyr Ser Lys Leu Thr Val Asp Lys Ser Arg Trp
            260                 265                 270

Gln Gln Gly Asn Val Phe Ser Cys Ser Val Met His Glu Gly Leu His
            275                 280                 285

Asn His Tyr Thr Gln Lys Ser Leu Ser Leu Ser Pro Gly Lys
        290                 295                 300

<210> SEQ ID NO 28
<211> LENGTH: 302
<212> TYPE: PRT
<213> ORGANISM: Artificial
<220> FEATURE:
<223> OTHER INFORMATION: N46FdrFc comprising N46 sequence of gp41,
      foldon sequence and rabbit Fc

<400> SEQUENCE: 28

Thr Leu Thr Val Gln Ala Arg Gln Leu Leu Ser Gly Ile Val Gln Gln
1               5                   10                  15

Gln Asn Asn Leu Leu Arg Ala Ile Glu Ala Gln Gln His Leu Leu Gln
            20                  25                  30

Leu Thr Val Trp Gly Ile Lys Gln Leu Gln Ala Arg Ile Leu Gly Tyr
            35                  40                  45

Ile Pro Glu Ala Pro Arg Asp Gly Gln Ala Tyr Val Arg Lys Asp Gly
        50                  55                  60

Glu Trp Val Leu Leu Ser Thr Phe Leu Arg Ser Asp Lys Thr His Thr
65                  70                  75                  80
```

```
Cys Pro Pro Cys Pro Ala Pro Glu Leu Leu Gly Gly Pro Ser Val Phe
            85                  90                  95

Leu Phe Pro Pro Lys Pro Lys Asp Thr Leu Met Ile Ser Arg Thr Pro
            100                 105                 110

Glu Val Thr Cys Val Val Val Asp Val Ser His Glu Asp Pro Glu Val
            115                 120                 125

Lys Phe Asn Trp Tyr Val Asp Gly Val Glu Val His Asn Ala Lys Thr
            130                 135                 140

Lys Pro Arg Glu Glu Gln Tyr Asn Ser Thr Tyr Arg Val Val Ser Val
145                 150                 155                 160

Leu Thr Val Leu His Gln Asp Trp Leu Asn Gly Lys Glu Tyr Lys Cys
            165                 170                 175

Lys Val Ser Asn Lys Ala Leu Pro Ala Pro Ile Glu Lys Thr Ile Ser
            180                 185                 190

Lys Ala Lys Gly Gln Pro Arg Glu Pro Gln Val Tyr Thr Leu Pro Pro
            195                 200                 205

Ser Arg Glu Glu Met Thr Lys Asn Gln Val Ser Leu Thr Cys Leu Val
            210                 215                 220

Lys Gly Phe Tyr Pro Ser Asp Ile Ala Val Glu Trp Glu Ser Asn Gly
225                 230                 235                 240

Gln Pro Glu Asn Asn Tyr Lys Thr Thr Pro Pro Val Leu Asp Ser Asp
            245                 250                 255

Gly Ser Phe Phe Leu Tyr Ser Lys Leu Thr Val Asp Lys Ser Arg Trp
            260                 265                 270

Gln Gln Gly Asn Val Phe Ser Cys Ser Val Met His Glu Gly Leu His
            275                 280                 285

Asn His Tyr Thr Gln Lys Ser Leu Ser Leu Ser Pro Gly Lys
            290                 295                 300

<210> SEQ ID NO 29
<211> LENGTH: 74
<212> TYPE: PRT
<213> ORGANISM: Artificial
<220> FEATURE:
<223> OTHER INFORMATION: IQN46 fusion protein comprising N46 sequence
      of gp41 and IQ sequence

<400> SEQUENCE: 29

Arg Met Lys Gln Ile Glu Asp Lys Ile Glu Glu Ile Glu Ser Lys Gln
1               5                   10                  15

Lys Lys Ile Glu Asn Glu Ile Ala Arg Ile Lys Lys Thr Leu Thr Val
            20                  25                  30

Gln Ala Arg Gln Leu Leu Ser Gly Ile Val Gln Gln Gln Asn Asn Leu
            35                  40                  45

Leu Arg Ala Ile Glu Ala Gln Gln His Leu Leu Gln Leu Thr Val Trp
        50                  55                  60

Gly Ile Lys Gln Leu Gln Ala Arg Ile Leu
65                  70

<210> SEQ ID NO 30
<211> LENGTH: 303
<212> TYPE: PRT
<213> ORGANISM: Artificial
<220> FEATURE:
<223> OTHER INFORMATION: IQN46hFc fusion protein comprising N46 sequence
      of gp41, IQ sequence and human Fc

<400> SEQUENCE: 30
```

-continued

```
Arg Met Lys Gln Ile Glu Asp Lys Ile Glu Ile Glu Ser Lys Gln
  1               5                  10                 15

Lys Lys Ile Glu Asn Glu Ile Ala Arg Ile Lys Lys Thr Leu Thr Val
             20                  25                  30

Gln Ala Arg Gln Leu Leu Ser Gly Ile Val Gln Gln Asn Asn Leu
             35                  40                  45

Leu Arg Ala Ile Glu Ala Gln Gln His Leu Leu Gln Leu Thr Val Trp
 50                  55                  60

Gly Ile Lys Gln Leu Gln Ala Arg Ile Leu Arg Ser Asp Lys Thr His
 65                  70                  75                  80

Thr Cys Pro Pro Cys Pro Ala Pro Glu Leu Leu Gly Gly Pro Ser Val
                 85                  90                  95

Phe Leu Phe Pro Pro Lys Pro Lys Asp Thr Leu Met Ile Ser Arg Thr
                100                 105                 110

Pro Glu Val Thr Cys Val Val Val Asp Val Ser His Glu Asp Pro Glu
                115                 120                 125

Val Lys Phe Asn Trp Tyr Val Asp Gly Val Glu Val His Asn Ala Lys
            130                 135                 140

Thr Lys Pro Arg Glu Glu Gln Tyr Asn Ser Thr Tyr Arg Val Val Ser
145                 150                 155                 160

Val Leu Thr Val Leu His Gln Asp Trp Leu Asn Gly Lys Glu Tyr Lys
                165                 170                 175

Cys Lys Val Ser Asn Lys Ala Leu Pro Ala Pro Ile Glu Lys Thr Ile
                180                 185                 190

Ser Lys Ala Lys Gly Gln Pro Arg Glu Pro Gln Val Tyr Thr Leu Pro
            195                 200                 205

Pro Ser Arg Glu Glu Met Thr Lys Asn Gln Val Ser Leu Thr Cys Leu
210                 215                 220

Val Lys Gly Phe Tyr Pro Ser Asp Ile Ala Val Glu Trp Glu Ser Asn
225                 230                 235                 240

Gly Gln Pro Glu Asn Asn Tyr Lys Thr Thr Pro Pro Val Leu Asp Ser
                245                 250                 255

Asp Gly Ser Phe Phe Leu Tyr Ser Lys Leu Thr Val Asp Lys Ser Arg
                260                 265                 270

Trp Gln Gln Gly Asn Val Phe Ser Cys Ser Val Met His Glu Gly Leu
            275                 280                 285

His Asn His Tyr Thr Gln Lys Ser Leu Ser Leu Ser Pro Gly Lys
        290                 295                 300
```

<210> SEQ ID NO 31
<211> LENGTH: 72
<212> TYPE: PRT
<213> ORGANISM: Artificial
<220> FEATURE:
<223> OTHER INFORMATION: IZN46 fusion protein comprising the N46
      sequence of gp41 and IZ sequence

<400> SEQUENCE: 31

```
Ile Lys Lys Glu Ile Glu Ala Ile Lys Lys Glu Gln Glu Ala Ile Lys
  1               5                  10                  15

Lys Lys Ile Glu Ala Ile Glu Lys Glu Ile Thr Leu Thr Val Gln Ala
             20                  25                  30

Arg Gln Leu Leu Ser Gly Ile Val Gln Gln Asn Asn Leu Leu Arg
             35                  40                  45

Ala Ile Glu Ala Gln Gln His Leu Leu Gln Leu Thr Val Trp Gly Ile
 50                  55                  60
```

```
Lys Gln Leu Gln Ala Arg Ile Leu
 65                  70
```

<210> SEQ ID NO 32
<211> LENGTH: 301
<212> TYPE: PRT
<213> ORGANISM: Artificial
<220> FEATURE:
<223> OTHER INFORMATION: IZN46hFc fusion protein comprising the N46
      sequence of gp41, IZ sequence and human Fc

<400> SEQUENCE: 32

```
Ile Lys Lys Glu Ile Glu Ala Ile Lys Lys Glu Gln Glu Ala Ile Lys
 1               5                  10                  15

Lys Lys Ile Glu Ala Ile Glu Lys Glu Ile Thr Leu Thr Val Gln Ala
            20                  25                  30

Arg Gln Leu Leu Ser Gly Ile Val Gln Gln Gln Asn Asn Leu Leu Arg
        35                  40                  45

Ala Ile Glu Ala Gln Gln His Leu Leu Gln Leu Thr Val Trp Gly Ile
    50                  55                  60

Lys Gln Leu Gln Ala Arg Ile Leu Arg Ser Asp Lys Thr His Thr Cys
 65                  70                  75                  80

Pro Pro Cys Pro Ala Pro Glu Leu Leu Gly Gly Pro Ser Val Phe Leu
                85                  90                  95

Phe Pro Pro Lys Pro Lys Asp Thr Leu Met Ile Ser Arg Thr Pro Glu
            100                 105                 110

Val Thr Cys Val Val Val Asp Val Ser His Glu Asp Pro Glu Val Lys
        115                 120                 125

Phe Asn Trp Tyr Val Asp Gly Val Glu Val His Asn Ala Lys Thr Lys
    130                 135                 140

Pro Arg Glu Glu Gln Tyr Asn Ser Thr Tyr Arg Val Val Ser Val Leu
145                 150                 155                 160

Thr Val Leu His Gln Asp Trp Leu Asn Gly Lys Glu Tyr Lys Cys Lys
                165                 170                 175

Val Ser Asn Lys Ala Leu Pro Ala Pro Ile Glu Lys Thr Ile Ser Lys
            180                 185                 190

Ala Lys Gly Gln Pro Arg Glu Pro Gln Val Tyr Thr Leu Pro Pro Ser
        195                 200                 205

Arg Glu Glu Met Thr Lys Asn Gln Val Ser Leu Thr Cys Leu Val Lys
    210                 215                 220

Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
                245                 250                 255

Ser Phe Phe Leu Tyr Ser Lys Leu Thr Val Asp Lys Ser Arg Trp Gln
            260                 265                 270

Gln Gly Asn Val Phe Ser Cys Ser Val Met His Glu Gly Leu His Asn
        275                 280                 285

His Tyr Thr Gln Lys Ser Leu Ser Leu Ser Pro Gly Lys
    290                 295                 300
```

<210> SEQ ID NO 33
<211> LENGTH: 26
<212> TYPE: DNA
<213> ORGANISM: Artificial
<220> FEATURE:
<223> OTHER INFORMATION: N46Fd forward primer

```
<400> SEQUENCE: 33
ccggaattcg acgctgacgg tacagg                                        26

<210> SEQ ID NO 34
<211> LENGTH: 42
<212> TYPE: DNA
<213> ORGANISM: Artificial
<220> FEATURE:
<223> OTHER INFORMATION: N46Fd reverse primer

<400> SEQUENCE: 34
ggaagatctt cagtggtggt ggtggtggtg cagaaaggta ga                      42

<210> SEQ ID NO 35
<211> LENGTH: 24
<212> TYPE: DNA
<213> ORGANISM: Artificial
<220> FEATURE:
<223> OTHER INFORMATION: N46FdhFc reverse primer

<400> SEQUENCE: 35
ggaagatctc agaaaggtag acag                                          24

<210> SEQ ID NO 36
<211> LENGTH: 81
<212> TYPE: DNA
<213> ORGANISM: Bacteriophage T4

<400> SEQUENCE: 36
ggctatattc cggaagcgcc gcgtgatggc caggcgtatg tgcgtaaaga tggcgaatgg   60
gtgctgctgt ctacctttct g                                             81
```